United States Patent [19]
Philipp et al.

[11] Patent Number: 5,580,842
[45] Date of Patent: Dec. 3, 1996

[54] N-AZINYL-N'-(HET)ARYLSULPHONYL-UREAS

[75] Inventors: Ulrich Philipp, Köln; Jörg Stetter, Wuppertal; Hans-Joachim Santel; Markus Dollinger, both of Leverkusen, all of Germany

[73] Assignee: Bayer Aktiengesellschaft, Leverkusen, Germany

[21] Appl. No.: 528,452

[22] Filed: Sep. 14, 1995

Related U.S. Application Data

[62] Division of Ser. No. 309,292, Sep. 20, 1994, Pat. No. 5,476,936.

[30] Foreign Application Priority Data

Sep. 27, 1993 [DE] Germany ............ 43 32 796.6
Oct. 29, 1993 [DE] Germany ............ 43 36 875.1

[51] Int. Cl.$^6$ ............ A01N 43/66; A01N 43/88; C07D 413/10; C07D 413/12
[52] U.S. Cl. ............ 504/213; 544/65
[58] Field of Search ............ 504/213; 544/198, 544/207, 209, 212, 65

[56] References Cited

U.S. PATENT DOCUMENTS 4,704,158 11/1987 Diehr et al. ............ 544/321
4,995,901 2/1991 Rorer ............ 544/207

FOREIGN PATENT DOCUMENTS 0173958 3/1986 European Pat. Off. ..
0301784 2/1989 European Pat. Off. ..

OTHER PUBLICATIONS

J. E. Johnson et al., J. Org. Chem., vol. 36(2) (1971), pp. 284–294.

*Primary Examiner*—John M. Ford
*Attorney, Agent, or Firm*—Sprung Horn Kramer & Woods

[57] ABSTRACT

N-azinyl-N'-(het)arylsulphonyl-ureas of the formula (I):

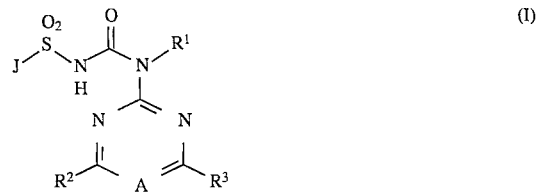

in which

J represents a 5,6-dihydro-[1,4,2]-dioxazin-3-ylaryl or -hetaryl radical;

A represents N or $CR^{11}$; and $R^{1-3 and 11}$ have the meanings given in the description; are useful as herbicides. Also, disclosed are several processes and intermediates for use therein in the preparation of the compounds of formula (I).

7 Claims, No Drawings

N-AZINYL-N'-(HET)ARYLSULPHONYL-UREAS

This application is a divisional of U.S. patent application Ser. No. 08/309,292, which was filed on Sep. 20, 1994, and issued as U.S. Pat. No. 5,476,936 on Dec. 19, 1995.

The invention relates to novel N-azinyl-N'-(het)arylsulphonyl-ureas, to processes and novel intermediates for their preparation, and to their use as herbicides.

It is already known that certain N-azinyl-N'-arylsulphonylureas having simple open-chain hydroxamic ester groups in the aryl moiety, such as, for example, N-(4,6-dimethylpyrimidin-2-yl)-N'-(2-methoxyaminocarbonyl-phenylsulphonyl)-urea and the corresponding -N'-(2-n-octyloxyaminocarbonylphenylsulphonyl)-urea, exhibit herbicidal properties (cf. DE-A-3 516 435; EP-A-173 958; U.S. Pat. No. 4,704,158). However, the herbicidal effect of these known compounds is not satisfactory in all respects.

In addition, certain herbicidally-active N-azinyl-N'-(het)arylsulphonyl-ureas have also become well known which are substituted in the (het)aryl moiety by O,O-dialkylated, likewise open-chain hydroxamic acid groups (cf. EP-A-301 784); by contrast, corresponding cyclic hydroxamic acid derivatives have not hitherto been described.

Novel N-azinyl-N'-(het)arylsulphonyl-ureas of the general formula (I)

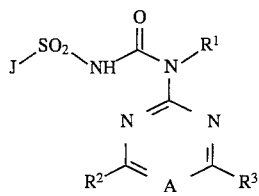

have now been found in which

A represents nitrogen or a $CR^{11}$ group, where
  $R^{11}$ represents hydrogen, alkyl, halogen and haloalkyl,
$R^1$ represents hydrogen or an optionally substituted radical from the series alkyl, alkoxy, alkoxyalkyl, alkenyl, alkinyl, cycloalkyl, cycloalkylalkyl, aralkyl and aryl,
$R^2$ represents hydrogen or halogen, or represents alkyl, alkoxy, alkylthio, alkylamino or dialkylamino having in each case 1 to 6 carbon atoms which are in each case optionally substituted by halogen,
$R^3$ represents hydrogen or halogen, or represents alkyl, alkoxy, alkylthio, alkylamino or dialkylamino having in each case 1 to 6 carbon atoms which are in each case optionally substituted by halogen,
J represents J-1 to J-4, where J-1 to J-4 have the following meanings:

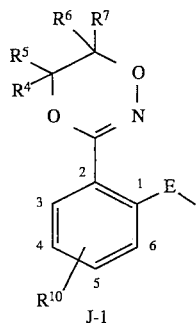 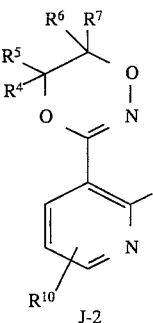

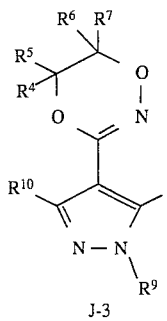 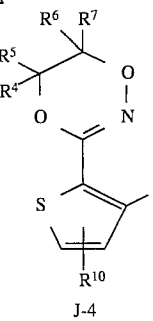

in which

E represents a direct linkage, alkylene, oxygen, alkylamino or sulphur,
$R^4$–$R^7$, independently of each other, represent hydrogen, halogen, cyano or thiocyanato, or represent alkyl, alkoxy, alkylthio, alkylsulphinyl, alkylsulphonyl, alkylamino, alkylcarbonyl, alkoxycarbonyl or alkylaminocarbonyl having in each case 1 to 3 carbon atoms which are in each case optionally substituted by halogen,
$R^8$ represents hydrogen or an optionally substituted radical from the series alkyl, alkenyl, alkinyl, cycloalkyl, cycloalkylalkyl, aralkyl and aryl, or represents a group $C(=O)R^9$, where
  $R^9$ represents hydrogen, optionally substituted alkyl, optionally substituted aryl, alkoxy, alkylamino or dialkylamino,
$R^{10}$ represents hydrogen, halogen, cyano or thiocyanato, or represents alkyl, alkoxy, alkylthio, alkylsulphinyl, alkylsulphonyl, alkylamino, alkylcarbonyl, alkoxycarbonyl or alkylaminocarbonyl having in each case 1 to 3 carbon atoms which are in each case optionally substituted by halogen, where, in the abovementioned radicals, the alkyl and alkylene groups can in each case contain 1 to 6 C atoms, the alkenyl and alkinyl groups in each case 2 to 6 C atoms, the cycloalkyl groups in each case 3 to 6 C atoms and the aryl groups in each case 6 or 10 C atoms, as well as salts of compounds of the formula (I).

Accordingly, the (5,6-dihydro-[1,4,2]-dioxazin-3-yl) radical, as a novel, heterocyclic substituent in the (het)aryl moiety of the N-azinyl-N'-(het)arylsulphonyl-ureas, is a characteristic structural feature of the novel sulphonylureas (I). The simple parent substance, which is not further substituted, of this compound class—(5,6-dihydro-[1,4,2]-dioxazin-3-yl)benzene, which can also be termed 3-phenyl-5H-1,4,2-dioxazine—is known (cf. J. E. Johnson et at., J. Org. Chem., Vol. 36 (2), (1971), pp. 284–294).

The novel N-azinyl-N'-(het)arylsulphonyl-ureas of the general formula (I) are obtained when (a) (het)arylsulphonamides of the general formula (II), $$J\text{—}SO_2\text{—}NH_2 \qquad \qquad (II),$$

in which

J has the abovementioned meanings, are reacted with N-azinyl carbamates of the formula (III),

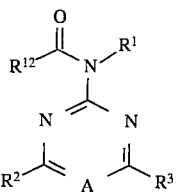    (III)

in which

A and $R^1$–$R^3$ have the abovementioned meanings, and $R^{12}$ represents alkyl or aryl, optionally in the presence of a diluent and optionally in the presence of a reaction auxiliary, or when (b) (het)arylsulphonyl isocyanates of the general formula (IV),

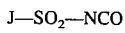    (IV)

in which

J has the abovementioned meanings, are reacted with aminoazines of the formula (V),

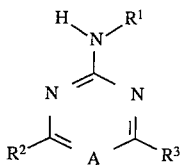    (V)

in which

A and $R^1$–$R^3$ have the abovementioned meanings, optionally in the presence of a diluent and optionally in the presence of a reaction auxiliary, or when (c) N-(het)arylsulphonyl carbamates of the general formula (VI),

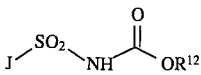    (VI)

in which

J and $R^{12}$ have the abovementioned meanings, are reacted with aminoazines of the formula (V),

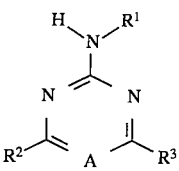    (V)

in which

A and $R^1$–$R^3$ have the abovementioned meanings, optionally in the presence of a diluent and optionally in the presence of a reaction auxiliary, and the products obtained by processes (a), (b) or (c) are optionally converted into salts in accordance with customary methods.

The novel N-azinyl-N'-(het)arylsulphonyl-ureas of the formula (I) are notable for strong herbicidal activity.

Surprisingly, the novel compounds of the formula (I) exhibit a considerably stronger effect than do the compounds N-(4,6-dimethylpyrimidin-2-yl)-N'-(2-methoxyaminocarbonyl-phenylsulphonyl)-urea and the corresponding -N'-(2-n-octyloxyaminocarbonyl-phenylsulphonyl)-urea, which are comparable from the point of view of structure and profile of activity.

The invention preferably relates to compounds of the formula (I)

in which

A represents nitrogen or a CH group, $R^1$ represents hydrogen or a radical from the series alkyl, alkoxy, alkoxyalkyl, alkenyl and alkinyl having in each case up to 3 carbon atoms which is optionally substituted by halogen, $R^2$ represents hydrogen or halogen, or represents alkyl, alkoxy, alkylthio, alkylamino or dialkylamino having in each case 1 to 3 carbon atoms in the alkyl radicals and which are in each case optionally substituted by halogen, $R^3$ represents hydrogen or halogen, or represents alkyl, alkoxy, alkylthio, alkylamino or dialkylamino having in each case 1 to 3 carbon atoms in the alkyl radicals and which are in each case optionally substituted by halogen, J represents J-1 to J-4, E represents a direct linkage, methylene, oxygen, alkylamino having 1 to 3 carbon atoms, or sulphur, $R^4$–$R^7$ independently of each other, represent hydrogen, halogen, cyano or thiocyanato, or represent alkyl, alkoxy, alkylthio, alkylsulphinyl, alkylsulphonyl, alkylamino, alkylcarbonyl, alkoxycarbonyl or alkylaminocarbonyl having in each case 1 to 3 carbon atoms in the alkyl radicals and which are in each case optionally substituted by halogen, $R^8$ represents hydrogen or an optionally substituted radical from the series $C_1$–$C_4$-alkyl, $C_3$–$C_6$-cycloalkyl, $C_7$–$C_{11}$-aralkyl and $C_6$–$C_{10}$-aryl, $R^{10}$ represents hydrogen, halogen, cyano or thiocyanato, or represents alkyl, alkoxy, alkylthio, alkylsulphinyl, alkylsulphonyl, alkylamino, alkylcarbonyl, alkoxycarbonyl or alkylaminocarbonyl having in each case 1 to 3 carbon atoms in the alkyl radicals and which are in each case optionally substituted by halogen.

The invention further relates preferably to salts which are obtained by customary processes from compounds of the formula (I) and bases, such as, for example, sodium, potassium or calcium hydroxide, hydride, amide and carbonate, sodium or potassium $C_1$–$C_4$-alkanolates, ammonia, $C_1$–$C_4$-alkylamines, di-($C_1$–$C_4$-alkyl)-amines or tri-($C_1$–$C_4$-alkyl)-amines.

The invention relates, in particular, to compounds of the formula (I), in which

A represents nitrogen or a CH group, $R^1$ represents hydrogen, methyl, ethyl, methoxy, methoxymethyl or ethoxy, $R^2$ represents hydrogen, chlorine, methyl, ethyl, tri fluoromethyl, methoxy, ethoxy, difluoromethoxy, methylthio, methylamino or dimethylamino, $R^3$ represents hydrogen, chlorine, methyl, ethyl, tri-fluoromethyl, methoxy, ethoxy, difluoromethoxy, methylthio, methylamino or dimethylamino, J represents J-1 to J-4, E represents a direct linkage, methylene, oxygen, $C_1$–$C_2$-alkylamino or sulphur, $R^4$–$R^7$, independently of each other, represent hydrogen, fluorine, chlorine or cyano, or represent methyl, methylthio, methylsulphinyl, methylsulphonyl, methoxycarbonyl and ethoxycarbonyl which are in each case optionally substituted by chlorine or fluorine, $R^8$ represents hydrogen, methyl, ethyl, phenyl or benzyl, $R^{10}$ represents hydrogen, fluorine, chlorine, bromine or cyano, or represents methyl, methoxy, ethoxy, methylthio, ethylthio, methylsulphinyl, ethylsulphinyl, methylsulphonyl, ethylsulphonyl, methylamino or dimethylamino which are in each case optionally substituted by chlorine or fluorine.

The above-listed general radical definitions, or those radical definitions listed in preference ranges, apply both to the end products of the formula (I) and also, in a corresponding manner, to the starting compounds or intermediates which are in each case required for the preparation. These radical definitions can be combined arbitrarily among themselves, that is also between the given preferred ranges.

The hydrocarbon radicals mentioned in the radical definitions, such as alkyl, alkenyl or alkinyl, also when in combinations with heteroatoms, such as in alkoxy, alkylthio or alkylamino, are straight-chain or branched, even when this is not expressly indicated.

If, for example, 2-(5,6-dihydro-[1,4,2]-dioxazin-3-yl) benzenesulphonamide and (4,6-dimethoxypyrimidin-2-yl)-phenyl carbamate are used as starting compounds for process variant (a), the course of the reaction can then be outlined by the following formula scheme:

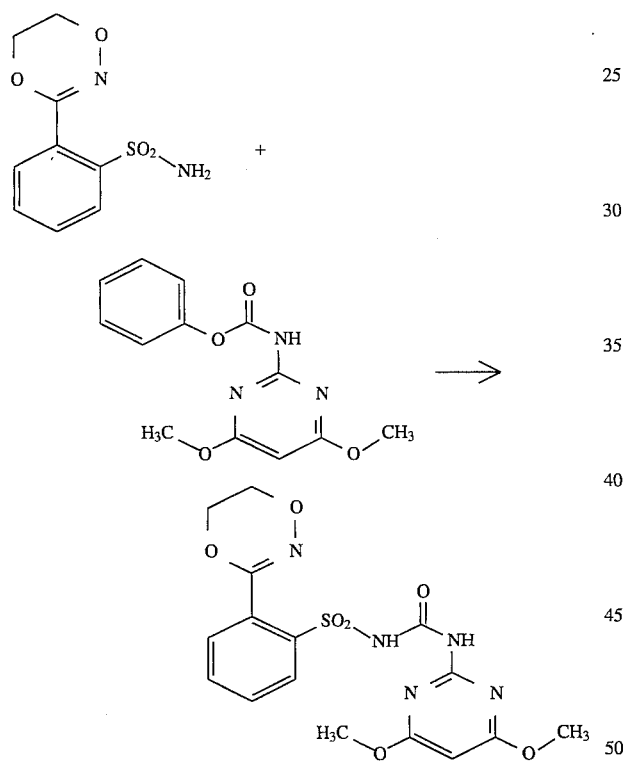

If, for example, 2-(5,6-dihydro-[1,4,2]-dioxazin-3-yl) benzenesulphonyl isocyanate and -amino-4,6-dimethoxypyrimidine are used as starting compounds for process variant (b), the course of the reaction can then be outlined by the following formula scheme:

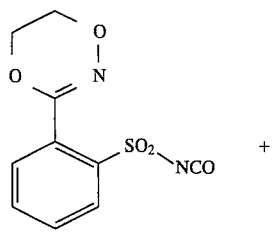

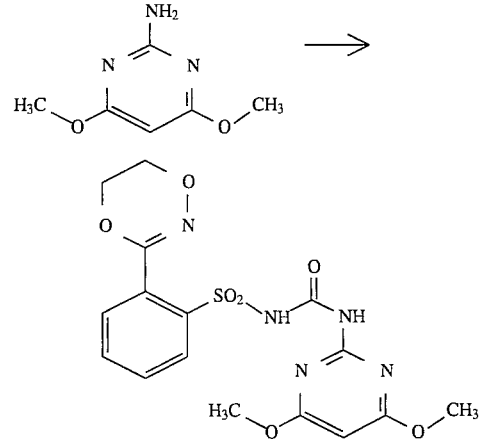

If, for example, N-(2-(5,6-dihydro-[1,4,2]-dioxazin-3-yl) benzenesulphonyl)-phenyl carbamate and 2-amino-4,6-dimethoxypyrimidine are used as starting compounds for process variant (c), the course of the reaction can then be outlined by the following formula scheme:

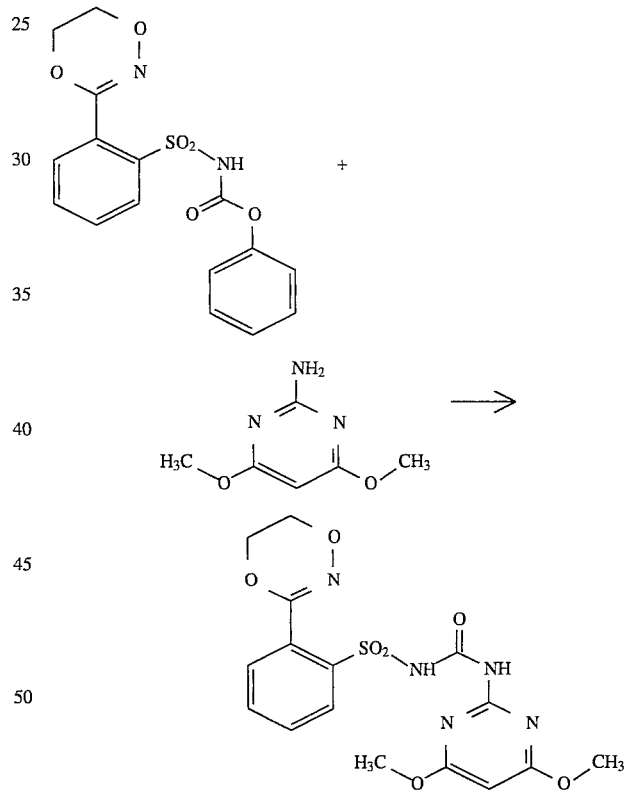

The (het)arylsulphonamides which are to be used as starting compounds for preparing compounds of the formula (I) in process (a) according to the invention are defined generally by formula (II). In formula (II), J preferably or in particular has those meanings which have already been indicated above, in connection with the description of the compounds of the formula (I) according to the invention, as being preferred or particularly preferred for J.

The following may be mentioned as examples of the compounds of the formula (II): 2-(5,6-dihydro-[1,4,2]-dioxazin-3-yl)benzenesulphonamide, 2-(5,6-dihydro-[1,4,2]-dioxazin-3-yl)-6-methyl-benzenesulphonamide, 2-(5,6-dihydro-[1,4,2]-dioxazin-3-yl)phenylmethanesulphonamide, 3-(5,6-dihydro-[1,4,2]-dioxazin-3-yl)pyridine-2-sulphonamide, 2-(5,6-dihydro-[1,4,2]-dioxazin-3-yl)thiophene-3-sulphonamide, 1-methyl-4-(5,6-dihydro-[1,4,2]-dioxazin-3-yl)pyrazole-5-sulphonamide, and 1-methyl-3-chloro-4-(5,6-dihydro-[1,4,2]-dioxazin-3-yl)pyrazole-5-sulphonamide.

The starting compounds of the formula (II) are still not known from the literature and, as novel compounds, are also a subject of the present invention.

Processes for preparing the compounds of the formula (II) are described further below [cf. processes (d) and (e)].

The N-azinyl carbamates which are also to be used as starting compounds in process (a) are defined generally by formula (III). In formula (III), A, $R^1$, $R^2$ and $R^3$ preferably or in particular have those meanings which have already been indicated above, in connection with the description of the compounds of formula (I) according to the invention, as being preferred or particularly preferred for A, $R^1$, $R^2$ and $R^3$. $R^{12}$ preferably represents $C_1$–$C_6$-alkyl or $C_6$–$C_{10}$-aryl, and particularly preferably represents $C_1$–$C_4$-alkyl or phenyl.

The following may be mentioned as examples of intermediates of the formula (III):
N-(4,6-dimethoxypyrimidin-2-yl)-phenyl carbamate, N-(4,6-diethoxypyrimidin-2-yl)phenyl carbamate, N-methyl-N-(4,6-dimethoxypyrimidin-2-yl)-phenyl carbamate, N-methoxymethyl-N-(4,6-dimethoxypyrimidin-2-yl)-phenyl carbamate, N-(4,6-dimethylpyrimidin-2-yl)-phenyl carbamate, N-(4,6-diethylpyrimidin-2-yl)-phenyl carbamate, N-[4,6-bis(difluoromethoxy)pyrimidin-2-yl]-phenyl carbamate, N-[4,6bis(dimethylamino)pyrimidin-2-yl]-phenyl carbamate, N-(4-methyl-6-ethyl pyrimidin-2-yl)-phenyl carbamate, N-(4-methoxy-6-chlorpyrimidin-2-yl)-phenyl carbamate, N-(4-ethoxy-6-methylaminotriazin-2-yl)-phenyl carbamate, N-(4-methoxy-6-methyltriazin-2-yl)-phenyl carbamate, N-(4-isopropoxy-6-chlortriazin-2-yl)-phenyl carbamate, N-(4-methoxy-6-chlortriazin-2-yl)-phenyl carbamate, N-[4-(2,2,2-trifluoroethoxy)-6-dimethylaminotriazin-2-yl]-phenylcarbamate, N-(4-trifluoromethyl-6-methoxytriazin-2-yl)-phenyl carbamate, N-(4-methylamino-6-chlortriazin-2-yl)phenyl carbamate, N-(4-methoxy-6-dimethylaminotriazin-2-yl)-phenyl carbamate, N-(4,6-dimethoxytriazin-2-yl)-phenyl carbamate, N-(4,6-diethoxytriazin-2-yl)-phenyl carbamate, N-(4,6-dimethyltriazin-2-yl)-phenyl carbamate, N-(4-methyl-6-chlorpyrimidin-2-yl)-phenyl carbamate, N-(4-methoxy-6-methylpyrimidin-2-yl)-phenyl carbamate, N-(4-methoxy-6-ethoxypyrimidin-2-yl)-phenyl carbamate, N-(4-methoxy-6-dimethylaminopyrimidin-2-yl)-phenyl carbamate, N-(4-ethoxy-6-chlorpyrimidin-2-yl)-phenyl-carbamate, N-(4-ethoxy-6-dimethylaminopyrimidin-2-yl)-phenylcarbamate, N-(4-methyl-6-dimethylaminopyrimidin-2-yl)-phenyl carbamate, N-(4-methyl-6-isopropoxypyrimidin-2-yl)-phenyl carbamate, N-(4-dimethylamino-6-chlorpyrimidin-2-yl)-phenyl carbamate, N-(4-methylamino-6-chlorpyrimidin-2-yl)-phenyl carbamate, N-(4-difluoromethoxy-6-methylpyrimidin-2-yl)-phenyl carbamate, N-[4-(2,2,2-trifluoroethoxy)-6-methylpyrimidin-2-yl]-phenyl carbamate, N-[4-(2,2,2-trifluoroethoxy)-6-chlorpyrimidin-2-yl]-phenyl carbamate.

The starting compounds of the formula (III) are known and/or can be prepared by processes which are known per se (cf. EP-238 070).

The (het)arylsulphonyl isocyanates to be used as starting compounds for preparing the compounds of the formula (I) in process (b) according to the invention are defined generally by formula (IV). In formula (IV), J preferably or in particular has those meanings which have already been indicated above, in connection with the description of the compounds of the formula (I) according to the invention, as being preferred or particularly preferred for J.

The following may be mentioned as examples of the starting compounds of the formula (IV):
2-(5,6-dihydro-[1,4,2]-dioxazin-3-yl)benzenesulphonyl isocyanate, 2-(5,6-dihydro-[1,4,2]-dioxazin-3-yl)-6-methylbenzenesulphonyl isocyanate, 2-(5,6-dihydro-[1,4,2]-dioxazin-3-yl)phenylmethanesulphonyl isocyanate, 3-(5,6-dihydro-[1,4,2]dioxazin-3-yl)-pyridine-2-sulphonylisocyanate, 2-(5,6-dihydro-[1,4,2]-dioxazin-3-sulphonyl isocyanate, 1-methyl-4-(5,6-dihydro-[1,4,2]-dioxazin-3-yl)-pyrazole-5-sulphonyl isocyanate, and 1-methyl-3-chloro-4-(5,6-dihydro-[1,4,2]-dioxazin-3-yl)-pyrazole-5-sulphonyl isocyanate.

The starting compounds of the formula (IV) are still not known from the literature and, as novel compounds, are also a subject of the present invention.

The novel (het)arylsulphonyl isocyanates of the formula (IV) are obtained by reacting (het)arylsulphonamides of the above formula (II) with phosgene in the presence of a diluent, such as, for example, chlorobenzene, and of reaction auxiliaries, such as, for example, butyl isocyanate and diazabicyclooctane (DABCO), at temperatures of between 0° C. and 200° C., preferably of between 20° C. and 160° C., and subsequently carefully distilling off the volatile components under reduced pressure (cf. EP-162 723).

The aminoazines which are further required as starting compounds for preparing compounds of the formula (I) in process (b) according to the invention are defined generally by formula (V). In formula (V), A, $R^1$, $R^2$ and $R^3$ preferably or in particular have those meanings which have already been indicated above, in connection with the description of the compounds of the formula (I) according to the invention, as being preferred or particularly preferred for A, $R^1$, $R^2$ and $R^3$.

The following may be mentioned as examples of the starting compounds of the formula (V):
2-amino-4,6-dimethoxypyrimidine, 2-amino-4,6-diethoxypyrimidine, 2-methylamino-4,6-dimethoxypyrimidine, 2-methoxymethylamino-4,6-dimethoxypyrimidine, 2-amino-4,6-dimethylpyrimidine, 2-amino-4,6-diethylpyrimidine, 2-amino-4,6-bis(difluormethoxy)pyrimidine, 2-amino-4,6-bis(dimethylamino)pyrimidine, 2-amino-4-methyl-6-ethylpyrimidine, 2-amino-4-methoxy-6-chlorpyrimidine, 2-amino-4-ethoxy-6-methylaminotriazine, 2-amino-4-methoxy-6-methyltriazine, 2-amino-4-isopropoxy-6-chlortriazine, 2-amino-4-methoxy-6-chlortriazine, 2-amino-4-(2,2,2-trifluoroethoxy)-6-dimethylaminotriazine, 2-amino-4-trifluoromethyl-6-methoxytriazine, 2-amino-4-methylamino-6-chlortriazine, 2-amino-4-methoxy-6-dimethylaminotriazine, 2-amino-4,6-dimethoxytriazine, 2-amino-4,6-diethoxytriazine, 2-amino-4,6-dimethyltriazine, 2-amino-4-methyl-6-chlorpyrimidine, 2-amino-4-methoxy-6-methylpyrimidine, 2-amino-4-methoxy-6-ethoxypyrimidine, 2-amino-4-methoxy-6-dimethylaminopyrimidine, 2-amino-4-ethoxy-6-chlorpyrimidine, 2-amino-4-ethoxy-6-dimethylaminopyrimidine, 2-amino-4-methyl-6-dimethylaminopyrimidine, 2-amino-4-methyl-6-isopropoxypyrimidine, 2-amino-4-dimethylamino-6-chlorpyrimidine, 2-amino-4-(2,2,2-trifluorethoxy)-6-chlorpyrimidine, 2-amino-4-methylamino-6-chlorpyrimidine, 2-amino-4-difluormethoxy-6-methylpyrimidine, 2-amino-4-(2,2,2-trifluorethoxy)-6-methylpyrimidine.

The starting compounds of the formula (V) are known and/or can be prepared by processes which are known per se (cf. Huaxue Shijie, 32(6), 254–7 (1991); JP-01 016 770; EP-246 984); some of these compounds are commercially obtainable as chemicals for use in syntheses.

The (het)arylsulphonyl carbamates to be used as starting compounds for preparing compounds of the formula (I) in process (c) according to the invention are defined generally by formula (VI). In formula (VI), J and $R^{12}$ prefer-ably or in particular have those meanings which have already been indicated above, in connection with the description of the compounds of the formulae (I) and (III) according to the invention, as being preferred or particularly preferred for J and $R^{12}$.

The following may be mentioned as examples of the starting compounds of the formula (VI):
N-(2-(5,6-dihydro-[1,4,2]-dioxazin-3-yl)benzenesulpho-nyl)-phenyl carbamate, N-(2-(5,6-dihydro-[1,4,2]-diox-azin-3-yl)-6-methyl-benzenesulphonyl)-phenyl carbamate, N-(2-(5,6-di-hydro-[1,4,2]-dioxazin-3-yl)phenylmethanesulphonyl)-phenyl carbamate, N-(3-(5,6-dihydro-[1,4,2]-dioxazin-3-yl)pyridine-2-sulphonyl)-phenyl carbamate, N-(2-(5,6-dihydro-[1,4,2]-dioxazin-3-yl)thiophene-3-sulphonyl)-phenyl carbamate, N-(1-methyl-4-(5,6-dihydro-[1,4,2]-dioxazin-3-yl)pyrazole-5-sulphonyl)-phenyl carbamate, and N-(1-methyl-3-chloro-4-(5,6-dihydro-[1,4,2]-dioxazin-3-yl)-pyrazole-5-sulphonyl)-phenyl carbamate.

The starting compounds of the formula (VI) are still not known from the literature and, as novel compounds, are also a subject of the present invention.

The novel (het)arylsulphonyl carbamates of the formula (VI) are obtained by reacting (het)arylsulphonamides of the above formula (II) with chloroformic esters in the presence of a diluent, such as, for example, dioxane or acetonitrile, and of reaction auxiliaries, such as, for example, pyridine, potassium carbonate or calcium carbonate, at temperatures of between 0° C. and 120° C., preferably of between 20° C. and 100° C., and subsequently carefully distilling off the volatile components under reduced pressure (cf. JP-04139170).

The aminoazines of the formula (V) which are further required as starting compounds in process (c) according to the invention have already been described in more detail above in process (b).

The novel, closely-related, starting compounds and intermediates of the formulae (II), (IV) and (VI), which have been described above, may, in summary, be designated "(het)arylsulphonyl compounds", and represented by the following formula (XI):

J—SO₂—G          (XI), in which
J has the meanings mentioned above for formula (I), and
G represents —NH₂, —N=C=O or —NH—CO OR$^{12}$, where $R^{12}$ has the abovementioned meaning.

It has, furthermore, been found that the abovedescribed (het)arylsulphonamides of the formula (II) are obtained when (d) (het)arylthiobenzyl ethers of the formula (VII),

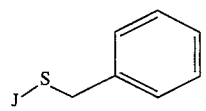

(VII)

in which
J has the meanings mentioned above for formula (I), is reacted with a chlorinating agent and water in the presence of an inert organic diluent, and optionally of a reaction auxiliary, and the sulphonyl chlorides thus obtained are reacted with ammonia or an ammonium salt in the presence of an inert organic diluent, and optionally of a reaction auxiliary (cf. EP-232 067, EP-451 468, U.S. Pat. No. 5,157,119).

If, for example, 1-benzylthio-2-(5,6-dihydro-[1,4,2]-dioxazin-3-yl)-benzene, chlorine, water and ammonia are used as starting compounds for process (d), the course of the reaction can then be outlined by the following reaction scheme:

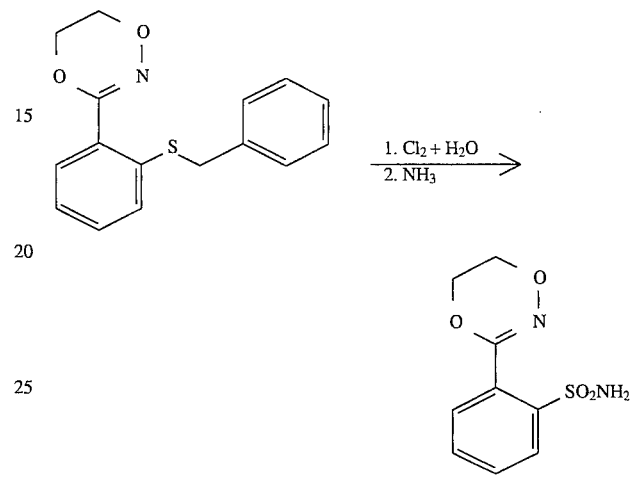

(e) Alternatively, the novel (het)arylsulphonamides of the formula (II) are obtained when (het)arylsulphonamides of the formula (VIII), in which T represents T-1 to T-4, where
T-1 to T-4 have the following meanings:

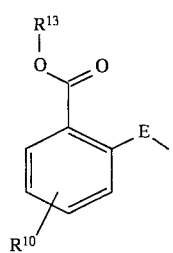

T-1

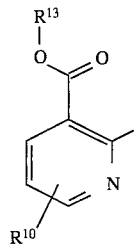

T-2

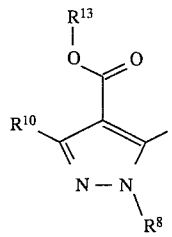

T-3

-continued

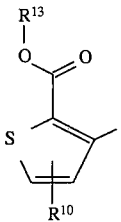
T-4 in which

E, $R^8$ and $R^{10}$ have the abovementioned meanings, and $R^{13}$ represents alkyl or aryl, and preferably represents $C_1$–$C_4$-alkyl or phenyl, are reacted with hydroxylamine hydrochloride and a substituted alkane of the formula (IX),

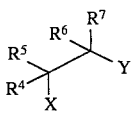
(IX)

in which $R^4$–$R^7$ have the abovementioned meanings, and

X and Y, independently of each other represent halogen, or represent alkylcarbonyloxy, arylcarbonyloxy, alkylsulphonyloxy or arylsulphonyloxy which are optionally substituted (preferably represent chlorine, bromine, iodine, $C_1$–$C_6$-alkylcarbonyloxy, $C_6$–$C_{12}$-arylcarbonyloxy, $C_1$–$C_6$-alkylsulphonyloxy or $C_6$–$C_{12}$-arylsulphonyloxy), optionally in the presence of an organic diluent and optionally in the presence of a reaction auxiliary (cf. J. Org. Chem., Vol. 36(2), pp. 284–294 (1971); JP-01 221 371).

If, for example, 1-methyl-4-ethoxycarbonylpyrazole-5-sulphonamide, hydroxylamine hydrochloride and 1,2-dibromoethane are used as starting compounds for process (e), the course of the reaction can then be outlined by the following reaction scheme:

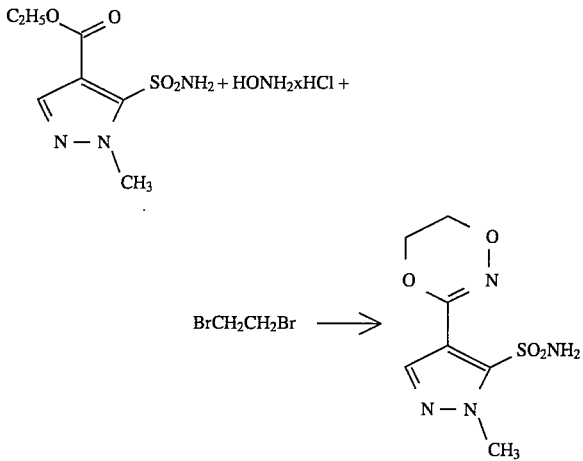

The (het)arylthiobenzyl ethers which are required as starting compounds for preparing compounds of the formula (II) in process (d) are defined generally by formula (VII). In formula (VII), J. preferably or in particular has those meanings which have already been indicated above, in connection with the description of the compounds of the formula (I) according to the invention, as being preferred or particularly preferred for J.

The following may be mentioned as examples of the intermediates of the formula (VII):

1-benzylthio-2-(5,6-dihydro-[1,2,4]-dioxazin-3-yl)-benzene, 1-benzylthio-2-(5,6-dihydro-[1,4,2]-dioxazin-3-yl)-6-methyl-benzene, 1-benzylthiomethyl-2-(5,6-dihydro[1,4,2]-dioxazin-3-yl)-benzene, 2-benzylthio-3-(5,6-dihydro-[1,4,2]-dioxazin-3-yl)pyridine, 1-methyl-5-benzylthio-4-(5,6-dihydro-[1,4,2]-dioxazin-3-yl)-pyrazole, methyl-3-chloro-5-benzylthio-4-(5,6-dihydro-[1,4,2]-dioxazin-3-yl)-pyrazole, 2-(5,6-dihydro-[1,4,2]-dioxazin-3-yl)-3-benzylthio-thiophene.

The starting compounds of the formula (VII) are still not known from the literature and, as novel compounds, are likewise a subject of the present invention.

A process for preparing the compounds of the formula (VII) is described further below (cf. process (f)).

The following may be mentioned as examples of the chlorinating agents which are also to be used as starting compounds in process (d): chlorine, sulphuryl chloride, alkali metal hypochlorite, chlorosulphonic acid.

The (het)arylsulphonamides to be used as starting compounds for preparing compounds of the formula (II) in process (e) according to the invention are defined generally by formula (VIII). In the formula (VIII), the group T has those preferred meanings which ensue from the above definitions of the radicals E, $R^8$, $R^{10}$ and $R^{13}$ contained therein.

The following may be mentioned as examples of the intermediates of the formula (VIII):

1-methyl-4-ethoxycarbonyl-pyrazole-5-sulphonamide,
1-methyl-3-chloro-4-ethoxycarbonyl-pyrazole-5-sulphonamide, 2-meth-oxycarbonylbenzenesulphonamide, (2-methoxycarbonylphenyl)methanesulphonamide,
3-methoxycarbonylpyridine-2-sulphonamide and 2-methoxycarbonylthiophene-3-sulphonamide.

The starting compounds of the formula (VIII) are known and/or can be prepared by processes which are known per se (cf., e.g., J. Heterocycl. Chem., 28(8), 1849–52, (1991); Pestic. Sci., 32(1), 91–104 (1991); Nippon Noyaku Gakkaishi, 15(4), 531–8 (1990); JP-63 051 394, JP-61 210 003; Eur. J. Med. Chem., 23(4), 329–34 (1988); ES-547 444, DE-2 706 859, DE-2 534 689).

The substituted alkanes which are additionally to be used as starting compounds in process (e) are defined generally by the formula (IX). In formula(IX), the substituents $R^4$, $R^5$, $R^6$ and $R^7$ preferably or in particular have those meanings which have already been indicated above, in connection with the description of the compounds of the formula (I), as being preferred or particularly preferred for $R^4$–$R^7$; the reactive, vicinal leaving groups X and Y have the preferred meanings which have already been indicated for formula (IX).

The following may be mentioned as examples of particularly suitable compounds of the formula (IX):

1,2-dichloroethane, 1,2-dibromoethane, 1,2-diiodoethane, 1,2-bis(methanesulphonyloxy)ethane, 1,2-bis-(trifluoromethanesulphonyloxy)ethane, 1,2-bis(trifluoroacetyloxy)ethane and 1,2-bis-(4-toluenesulphonyloxy)ethane.

The starting compounds of the formula (IX) are known without exception and some of them are commercially available as chemicals for use in syntheses.

Finally, it has been found that the novel (het)arylthiobenzyl ethers of the above formula (VII), which are required for process (d), are obtained when (f) (Het)arylthiobenzylcarboxylic esters of the formula (X)

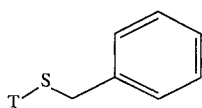

in which

T has the meanings indicated above for process (e), are reacted with hydroxylamine hydrochloride and a substituted alkane of the formula (IX),

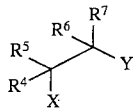

in which $R^4$–$R^7$ have the above-indicated meanings, and

X and Y, independently of each other, represent halogen, or represent alkylcarbonyloxy, arylcarbonyloxy, alkylsulphonyloxy or arylsulphonyloxy, which are optionally substituted (preferably represent chlorine, bromine, iodine, $C_1$–$C_6$-alkylcarbonyloxy, $C_6$–$C_{12}$-arylcarbonyloxy, $C_1$–$C_6$-alkylsulphonyloxy or $C_6$–$C_{12}$-arylsulphonyloxy), optionally in the presence of an organic diluent and optionally in the presence of a reaction auxiliary.

If, for example, methyl 2-benzylmercaptobenzoate, hydroxylamine hydrochloride and 1,2-dibromoethane are used as starting compounds for process (f), the course of the reaction can then be outlined by the following reaction scheme:

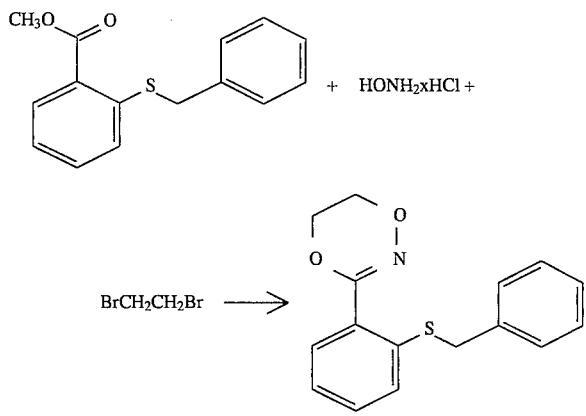

The (het)arylthiobenzylcarboxylic esters which are required as starting compounds for preparing compounds of the formula (VII) in process (f) according to the invention are defined generally by formula (X); that which has been said above in relation to process (e) applies for the meaning of the group T.

The following may be mentioned as examples of the intermediates of the formula (X):

methyl 2-benzylmercaptobenzoate, methyl 2-benzylmercapto-6-methyl-benzoate, methyl (2-benzylmercaptophenyl)-acetate, methyl 2-benzylmercaptopyridine-3-carboxylate, methyl 1-methyl-5-benzylmercaptopyrazole-4-carboxylate, methyl 1-methyl-3-chloro-5-benzylmercaptopyrazole-4-carboxylate and methyl 3-benzyl-mercaptothiophene-2-carboxylate.

The starting compounds of the formula (X) are known and/or can be prepared by processes which are known per se (cf., e.g., Chem. Pharm. Bull., 34(2), 540–9 (1986), J. Hetero-cycl. Chem. 15(3), 513–14 (1978)).

The substituted alkanes of the formula (IX) which are additionally to be used as starting compounds in process (f) have already been described above in more detail for process (e).

The processes (a), (b) and (c) according to the invention for preparing the novel compounds (I), the processes (d) and (e) according to the invention for preparing the novel intermediates of the formula (II), and the process (f) according to the invention for preparing the novel intermediates of the formula (VII), are preferably carried out using diluents. In this context, practically all inert organic solvents are suitable for use as diluents. These preferably include—except for process (d)—aliphatic and aromatic, optionally halogenated hydrocarbons, such as pentane, hexane, heptane, cyclohexane, petroleum ether, benzinc, ligroin, benzene, toluene, xylene, methylene chloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, as well as dimethyl sulphoxide, tetramethylene sulphone and hexamethylphosphoric triamide.

In the main, it is only the previously mentioned chlorinated solvents which are suitable for use as diluents in the chlorination process (d).

The processes (a), (e) and (f) according to the invention are optionally carried out in the presence of a reaction auxiliary. These preferably include basic organic nitrogen compounds, such as, for example, trimethylamine, triethylamine, N,N-dimethylaniline, N,N-dimethylbenzylamine, pyridine, 4-dimethylaminopyridine, diazabicyclooctane (DABCO), diazabicyclononene (DBN) and diazabicycloundecene (DBU), as well as inorganic bases, such as, for example, sodium hydride, potassium hydride, sodium carbonate, potassium carbonate, calcium carbonate, potassium hydroxide, sodium hydroxide and calcium hydroxide.

The processes (b) and (c) according to the invention are also optionally carried out in the presence of a reaction auxiliary. Basic organic nitrogen compounds, such as, for example, trimethylamine, triethylamine, N,N-dimethylaniline, N,N-dimethylbenzylamine, pyridine, 4-dimethylaminopyridine, diazabicyclooctane (DABCO), diazabicyclononene (DBN) and diazabicycloundecene (DBU), are suitable and preferred for these processes.

The chlorinating process (d) can likewise be carried out in the presence of a reaction auxiliary. Certain mineral and organic acids, such as, for example, hydrochloric acid, dilute sulphuric acid, phosphoric acid, acetic acid or propionic acid, and, in addition, acidic salts, such as, for example, $NaH_2PO_4$, are particularly suitable for this process.

In processes (a) to (f), the reaction temperatures may in each case be varied over a relatively wide range. Thus in process (a), temperatures of between 0° C. and 150° C., preferably of between 10° C. and 80° C., are generally employed;

in process (b), temperatures of between 0° C. and 150° C., preferably of between 20° C. and 100° C., are generally employed;

in process (c), temperatures of between 0° C. and 150° C., preferably of between 20° C. and 100° C., are likewise generally employed;

in process (d), temperatures of between −20° C. and +40° C., preferably of between −20° C. and +30° C., are generally employed;

in process (e), temperatures of between 0° C. and 150° C., preferably of between 10° C. and 80° C., are generally employed, and in process (f), temperatures of between 0° C. and 150° C., preferably of between 10° C. and 80° C., are also generally employed.

The processes (a) to (f) are generally carried out under atmospheric pressure. However, it is in each case also possible to use elevated or reduced pressure.

In order to carry out processes (a) to (f) according to the invention, the starting compounds which are in each case required are employed in approximately equimolar quantities. However, it is also possible to use one of the two components which are in each case employed in a relatively large excess. In general, the reactions are carded out in a suitable diluent and, where appropriate, with the addition of a reaction auxiliary, and the reaction mixture is stirred for several hours at the temperature which is in each case required. In each of the processes according to the invention, working up is effected in accordance with customary methods.

Where appropriate, salts may be prepared from the compounds of the general formula (I) according to the invention. Such salts are obtained in a simple manner in accordance with customary salt-formation methods, for example by dissolving or dispersing a compound of the formula (I) in a suitable diluent, such as, for example, methylene chloride, acetone, tert-butyl methyl ether or toluene, and adding a suitable base. The salts may then be isolated—where appropriate after a relatively long period of stirring—by concentrating or by filtering off with suction (cf. the preparation examples).

The active compounds according to the invention can be used as defoliants, desiccants, agents for destroying broadleaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Sacchamm, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hop fields, on ornamental lawns and sports turf and on pasture land and for the selective combating of weeds in annual cultures.

The compounds of the formula (I) according to the invention can suitably be used for selectively controlling monocotyledonous and dicotyledonous weeds in different cultures, in some cases, e.g. in wheat, both in the preemergence process and in the postemergence process.

The active compounds can be converted into the customary formulations, such as solutions, emulsions, suspensions, powders, foams, pastes, granules, aerosols, natural and synthetic materials impregnated with active compound, and very fine capsules in polymeric substances.

These formulations are produced in a known manner, for example by mixing the active compounds with extenders, that is, liquid solvents, liquified gases under pressure, and/or solid carriers, optionally with use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclo-hexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethyl-formamide or dimethyl sulphoxide, as well as water.

As solid carriers there are suitable: for example ammonium salts and ground natural minerals, such as kaolins, days, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydro-lysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxyphenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, diallate, EPTC, esprocarb, molinate, prosulfocarb, thiobencarb and triallate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in customary manner, for example by watering, spraying, atomizing or scattering.

The active compounds according to the invention can be applied either before or after emergence of the plants. They can also be incorporated into the soil before sowing.

The amount of active compound used can vary within a relatively large range. It depends essentially on the nature of the desired effect. In general, the amounts used are between 10 g and 10 kg of active compound per hectare of soil surface, preferably between 50 g and 5 kg per hectare.

The preparation and use of the active compounds according to the invention can be seen from the following examples.

PREPARATION EXAMPLES

EXAMPLE I-1

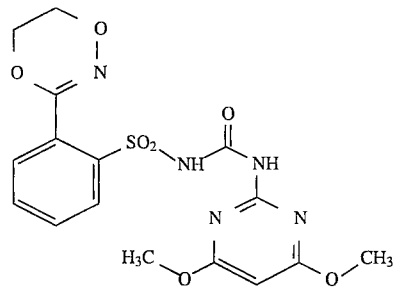

Process (a)

0.79 g (0.033 mol) of sodium hydride are added under argon to a mixture of 4.0 g (0.017 mol) of 2-(5,6-dihydro-[1,4,2]-dioxazin-3-yl)benzenesulphonamide and 4.6 g (0.017 mol) of 2-phenoxycarbonylamino-4,6-dimethoxypyrimidine in 20 ml of absolute acetonitrile, and the mixture is stirred at room temperature for 18 hours. The precipitate is filtered off with suction and stirred up with a 20% solution of sodium dihydrogen phosphate. The precipitate is filtered off with suction and dried under high vacuum. 3.9 g (56% of theory) of N-(4,6-dimethoxypyrimidin-2-yl)-N'-(2-(5,6-dihydro-[1,4,2]-dioxazin-3-yl)benzenesulphonyl)urea are obtained with a melting point of 189° C.

The additional compounds of the formula (I) listed in Tables 1, 2, 3 and 4 below can also, for example, be prepared in analogy with Example I-1 and in correspondence with the general description of the preparation processes according to the invention.

Abbreviations: m.p.:=melting point decomp. or d.=with decomposition.

(+) The melting point (m.p.) which is given relates in each case to the corresponding sodium salt.

TABLE 1

Examples of compounds of the formula (I) having $R^4 = R^5 = R^6 = R^7 = H$ and $CH_3$: and $R^{10} = H$:

| Ex. No. | J | E | $R^1$ | A | $R^2$ | $R^3$ | m.p. (°C.) |
|---|---|---|---|---|---|---|---|
| I-1 | J-1 | — | H | CH | $OCH_3$ | $OCH_3$ | 224 163$^{(+)}$ |
| I-2 | J-1 | — | H | CH | $OCH_3$ | $OC_2H_5$ | 176 70–71$^{(+)}$ |
| I-3 | J-1 | — | H | CH | $OCH_3$ | $CH_3$ | 145–146 157–163$^{(+)}$ |
| I-4 | J-1 | — | H | CH | $OCH_3$ | $C_2H_5$ | |
| I-5 | J-1 | — | H | CH | $OCH_3$ | $CF_3$ | |
| I-6 | J-1 | — | H | CH | $OCH_3$ | $OCF_2H$ | |
| I-7 | J-1 | — | H | CH | $OCH_3$ | $NHCH_3$ | |
| I-8 | J-1 | — | H | CH | $OCH_3$ | $N(CH_3)_2$ | 192–193 |
| I-9 | J-1 | — | H | CH | $OCH_3$ | Cl | 100–103 172–174$^{(+)}$ |
| I-10 | J-1 | — | H | CH | $OC_2H_5$ | $OC_2H_5$ | |
| I-11 | J-1 | — | H | CH | $OC_2H_5$ | $CH_3$ | |
| I-12 | J-1 | — | H | CH | $OC_2H_5$ | $C_2H_5$ | |
| I-13 | J-1 | — | H | CH | $OC_2H_5$ | $CF_3$ | |
| I-14 | J-1 | — | H | CH | $OC_2H_5$ | $OCF_2H$ | |
| I-15 | J-1 | — | H | CH | $OC_2H_5$ | $NHCH_3$ | |

TABLE 1-continued

Examples of compounds of the formula (I) having
$R^4 = R^5 = R^6 = R^7 = H$ and $CH_3$: and $R^{10} = H$:

| Ex. No. | J | E | $R^1$ | A | $R^2$ | $R^3$ | m.p. (°C.) |
|---|---|---|---|---|---|---|---|
| I-16 | J-1 | — | H | CH | $OC_2H_5$ | $N(CH_3)_2$ | |
| I-17 | J-1 | — | H | CH | $OC_2H_5$ | Cl | 119–122 |
| I-18 | J-1 | — | H | CH | $CH_3$ | $CH_3$ | 186–187 172–173[(+)] |
| I-19 | J-1 | — | H | CH | $CH_3$ | $C_2H_5$ | |
| I-20 | J-1 | — | H | CH | $CH_3$ | $CF_3$ | |
| I-21 | J-1 | — | H | CH | $CH_3$ | $OCF_2H$ | |
| I-22 | J-1 | — | H | CH | $CH_3$ | $NHCH_3$ | |
| I-23 | J-1 | — | H | CH | $CH_3$ | $N(CH_3)_2$ | 133 99[(+)] |
| I-24 | J-1 | — | H | CH | $CH_3$ | Cl | 146 110–111 |
| I-25 | J-1 | — | H | CH | $C_2H_5$ | $C_2H_5$ | |
| I-26 | J-1 | — | H | CH | $C_2H_5$ | $CF_3$ | |
| I-27 | J-1 | — | H | CH | $C_2H_5$ | $OCF_2H$ | |
| I-28 | J-1 | — | H | CH | $C_2H_5$ | $NHCH_3$ | |
| I-29 | J-1 | — | H | CH | $C_2H_5$ | Cl | |
| I-30 | J-1 | — | H | CH | $CF_3$ | $CF_3$ | |
| I-31 | J-1 | — | H | CH | $CF_3$ | $OCF_2H$ | |
| I-32 | J-1 | — | H | CH | $CF_3$ | $NHCH_3$ | |
| I-33 | J-1 | — | H | CH | $CF_3$ | $N(CH_3)_2$ | |
| I-34 | J-1 | — | H | CH | $CF_3$ | Cl | |
| I-35 | J-1 | — | H | CH | $OCF_2H$ | $OCF_2H$ | |
| I-36 | J-1 | — | H | CH | $OCF_2H$ | $NHCH_3$ | |
| I-37 | J-1 | — | H | CH | $OCF_2H$ | $N(CH_3)_2$ | |
| I-38 | J-1 | — | H | CH | $OCF_2H$ | Cl | |
| I-39 | J-1 | — | H | CH | $NHCH_3$ | $NHCH_3$ | |
| I-40 | J-1 | — | H | CH | $NHCH_3$ | $N(CH_3)_2$ | |
| I-41 | J-1 | — | H | CH | $NHCH_3$ | Cl | |
| I-42 | J-1 | — | H | CH | $N(CH_3)_2$ | $N(CH_3)_2$ | |
| I-43 | J-1 | — | H | CH | $N(CH_3)_2$ | Cl | |
| I-44 | J-1 | — | H | CH | Cl | Cl | |
| I-45 | J-1 | — | H | N | $OCH_3$ | $OCH_3$ | 193 |
| I-46 | J-1 | — | H | N | $OCH_3$ | $OC_2H_5$ | |
| I-47 | J-1 | — | H | N | $OCH_3$ | $CH_3$ | 190–192 178[(+)] |
| I-48 | J-1 | — | H | N | $OCH_3$ | $C_2H_5$ | |
| I-49 | J-1 | — | H | N | $OCH_3$ | $CF_3$ | |
| I-50 | J-1 | — | H | N | $OCH_3$ | $OCF_2H$ | |
| I-51 | J-1 | — | H | N | $OCH_3$ | $NHCH_3$ | |
| I-52 | J-1 | — | H | N | $OCH_3$ | $N(CH_3)_2$ | 91–93 175[(+)] |
| I-53 | J-1 | — | H | N | $OCH_3$ | Cl | |
| I-54 | J-1 | — | H | N | $OC_2H_5$ | $OC_2H_5$ | |
| I-55 | J-1 | — | H | N | $OC_2H_5$ | $CH_3$ | |
| I-56 | J-1 | — | H | N | $OC_2H_5$ | $C_2H_5$ | |
| I-57 | J-1 | — | H | N | $OC_2H_5$ | $CF_3$ | |
| I-58 | J-1 | — | H | N | $OC_2H_5$ | $OCF_2H$ | |
| I-59 | J-1 | — | H | N | $OC_2H_5$ | $NHCH_3$ | |
| I-60 | J-1 | — | H | N | $OC_2H_5$ | $N(CH_3)_2$ | |
| I-61 | J-1 | — | H | N | $OC_2H_5$ | Cl | |
| I-62 | J-1 | — | H | N | $CH_3$ | $CH_3$ | 179–181 168–172[(+)] |
| I-63 | J-1 | — | H | N | $CH_3$ | $C_2H_5$ | |
| I-64 | J-1 | — | H | N | $CH_3$ | $CF_3$ | |
| I-65 | J-1 | — | H | N | $CH_3$ | $OCF_2H$ | |
| I-66 | J-1 | — | H | N | $CH_3$ | $NHCH_3$ | |
| I-67 | J-1 | — | H | N | $CH_3$ | $N(CH_3)_2$ | |
| I-68 | J-1 | — | H | N | $CH_3$ | Cl | |
| I-69 | J-1 | — | H | N | $C_2H_5$ | $C_2H_5$ | |
| I-70 | J-1 | — | H | N | $C_2H_5$ | $CF_3$ | |
| I-71 | J-1 | — | H | N | $C_2H_5$ | $OCF_2H$ | |
| I-72 | J-1 | — | H | N | $C_2H_5$ | $NHCH_3$ | |
| I-73 | J-1 | — | H | N | $C_2H_5$ | Cl | |
| I-74 | J-1 | — | H | N | $CF_3$ | $CF_3$ | |
| I-75 | J-1 | — | H | N | CF3 | $OCF_2H$ | |
| I-76 | J-1 | — | H | N | CF3 | $NHCH_3$ | |
| I-77 | J-1 | — | H | N | CF3 | $N(CH_3)_2$ | |
| I-78 | J-1 | — | H | N | CF3 | Cl | |
| I-79 | J-1 | — | H | N | $OCF_2H$ | $OCF_2H$ | |
| I-80 | J-1 | — | H | N | $OCF_2H$ | $NHCH_3$ | |
| I-81 | J-1 | — | H | N | $OCF_2H$ | $N(CH_3)_2$ | |
| I-82 | J-1 | — | H | N | $OCF_2H$ | Cl | |
| I-83 | J-1 | — | H | N | $NHCH_3$ | $NHCH_3$ | |
| I-84 | J-1 | — | H | N | $NHCH_3$ | $N(CH_3)_2$ | |
| I-85 | J-1 | — | H | N | $NHCH_3$ | Cl | |
| I-86 | J-1 | — | H | N | $N(CH_3)_2$ | $N(CH_3)_2$ | |
| I-87 | J-1 | — | H | N | $N(CH_3)_2$ | Cl | |
| I-88 | J-1 | — | H | N | Cl | Cl | |
| I-89 | J-1 | — | $CH_3$ | N | $OCH_3$ | $OCH_3$ | 151–152[(+)] |
| I-90 | J-1 | — | $CH_3$ | N | $OCH_3$ | $OC_2H_5$ | |
| I-91 | J-1 | — | $CH_3$ | N | $OCH_3$ | $CH_3$ | |
| I-92 | J-1 | — | $CH_3$ | N | $OCH_3$ | $C_2H_5$ | |
| I-93 | J-1 | — | $CH_3$ | N | $OCH_3$ | $CF_3$ | |
| I-94 | J-1 | — | $CH_3$ | N | $OCH_3$ | $OCF_2H$ | |
| I-95 | J-1 | — | $CH_3$ | N | $OCH_3$ | $NHCH_3$ | |
| I-96 | J-1 | — | $CH_3$ | N | $OCH_3$ | $N(CH_3)_2$ | |
| I-97 | J-1 | — | $CH_3$ | N | $OCH_3$ | Cl | |
| I-98 | J-1 | — | $CH_3$ | N | $OC_2H_5$ | $OC_2H_5$ | |
| I-99 | J-1 | — | $CH_3$ | N | $OC_2H_5$ | $CH_3$ | |
| I-100 | J-1 | — | $CH_3$ | N | $OC_2H_5$ | $C_2H_5$ | |
| I-101 | J-1 | — | $CH_3$ | N | $OC_2H_5$ | $CF_3$ | |
| I-102 | J-1 | — | $CH_3$ | N | $OC_2H_5$ | $OCF_2H$ | |
| I-103 | J-1 | — | $CH_3$ | N | $OC_2H_5$ | $NHCH_3$ | |
| I-104 | J-1 | — | $CH_3$ | N | $OC_2H_5$ | $N(CH_3)_2$ | |
| I-105 | J-1 | — | $CH_3$ | N | $OC_2H_5$ | Cl | |
| I-106 | J-1 | — | $CH_3$ | N | $CH_3$ | $CH_3$ | |
| I-107 | J-1 | — | $CH_3$ | N | $CH_3$ | $C_2H_5$ | |
| I-108 | J-1 | — | $CH_3$ | N | $CH_3$ | $CF_3$ | |
| I-109 | J-1 | — | $CH_3$ | N | $CH_3$ | $OCF_2H$ | |
| I-110 | J-1 | — | $CH_3$ | N | $CH_3$ | $NHCH_3$ | |
| I-111 | J-1 | — | $CH_3$ | N | $CH_3$ | $N(CH_3)_2$ | |
| I-112 | J-1 | — | $CH_3$ | N | $CH_3$ | Cl | |
| I-113 | J-1 | — | $CH_3$ | N | $C_2H_5$ | $C_2H_5$ | |
| I-114 | J-1 | — | $CH_3$ | N | $C_2H_5$ | $CF_3$ | |
| I-115 | J-1 | — | $CH_3$ | N | $C_2H_5$ | $OCF_2H$ | |
| I-116 | J-1 | — | $CH_3$ | N | $C_2H_5$ | $NHCH_3$ | |
| I-117 | J-1 | — | $CH_3$ | N | $C_2H_5$ | Cl | |
| I-118 | J-1 | — | $CH_3$ | N | $CF_3$ | $CF_3$ | |
| I-119 | J-1 | — | $CH_3$ | N | $CF_3$ | $OCF_2H$ | |
| I-120 | J-1 | — | $CH_3$ | N | $CF_3$ | $NHCH_3$ | |
| I-121 | J-1 | — | $CH_3$ | N | $CF_3$ | $N(CH_3)_2$ | |
| I-122 | J-1 | — | $CH_3$ | N | $CF_3$ | Cl | |
| I-123 | J-1 | — | $CH_3$ | N | $OCF_2H$ | $OCF_2H$ | |
| I-124 | J-1 | — | $CH_3$ | N | $OCF_2H$ | $NHCH_3$ | |
| I-125 | J-1 | — | $CH_3$ | N | $OCF_2H$ | $N(CH_3)_2$ | |
| I-126 | J-1 | — | $CH_3$ | N | $OCF_2H$ | Cl | |
| I-127 | J-1 | — | $CH_3$ | N | $NHCH_3$ | $NHCH_3$ | |
| I-128 | J-1 | — | $CH_3$ | N | $NHCH_3$ | $N(CH_3)_2$ | |
| I-129 | J-1 | — | $CH_3$ | N | $NHCH_3$ | Cl | |
| I-130 | J-1 | — | $CH_3$ | N | $N(CH_3)_2$ | $N(CH_3)_2$ | |
| I-131 | J-1 | — | $CH_3$ | N | $N(CH_3)_2$ | Cl | |
| I-132 | J-1 | — | $CH_3$ | N | Cl | Cl | |
| I-133 | J-1 | $CH_2$— | H | CH | $OCH_3$ | $OCH_3$ | |
| I-134 | J-1 | $CH_2$— | H | CH | $OCH_3$ | $OC_2H_5$ | |
| I-135 | J-1 | $CH_2$— | H | CH | $OCH_3$ | $CH_3$ | |
| I-136 | J-1 | $CH_2$— | H | CH | $OCH_3$ | $C_2H_5$ | |
| I-137 | J-1 | $CH_2$— | H | CH | $OCH_3$ | $CF_3$ | |
| I-138 | J-1 | $CH_2$— | H | CH | $OCH_3$ | $OCF_2H$ | |
| I-139 | J-1 | $CH_2$— | H | CH | $OCH_3$ | $NHCH_3$ | |
| I-140 | J-1 | $CH_2$— | H | CH | $OCH_3$ | $N(CH_3)_2$ | |
| I-141 | J-1 | $CH_2$— | H | CH | $OCH_3$ | Cl | |
| I-142 | J-1 | $CH_2$— | H | CH | $OC_2H_5$ | $OC_2H_5$ | |
| I-143 | J-1 | $CH_2$— | H | CH | $OC_2H_5$ | $CH_3$ | |
| I-144 | J-1 | $CH_2$— | H | CH | $OC_2H_5$ | $C_2H_5$ | |
| I-145 | J-1 | $CH_2$— | H | CH | $OC_2H_5$ | $CF_3$ | |
| I-146 | J-1 | $CH_2$— | H | CH | $OC_2H_5$ | $OCF_2H$ | |
| I-147 | J-1 | $CH_2$— | H | CH | $OC_2H_5$ | $NHCH_3$ | |
| I-148 | J-1 | $CH_2$— | H | CH | $OC_2H_5$ | $N(CH_3)_2$ | |
| I-149 | J-1 | $CH_2$— | H | CH | $OC_2H_5$ | Cl | |
| I-150 | J-1 | $CH_2$— | H | CH | $CH_3$ | $CH_3$ | |
| I-151 | J-1 | $CH_2$— | H | CH | $CH_3$ | $C_2H_5$ | |
| I-152 | J-1 | $CH_2$— | H | CH | $CH_3$ | $CF_3$ | |
| I-153 | J-1 | $CH_2$— | H | CH | $CH_3$ | $OCF_2H$ | |
| I-154 | J-1 | $CH_2$— | H | CH | $CH_3$ | $NHCH_3$ | |
| I-155 | J-1 | $CH_2$— | H | CH | $CH_3$ | $N(CH_3)_2$ | |

TABLE 1-continued

Examples of compounds of the formula (I) having
$R^4 = R^5 = R^6 = R^7 = H$ and $CH_3$: and $R^{10} = H$:

| Ex. No. | J | E | $R^1$ | A | $R^2$ | $R^3$ | m.p. (°C.) |
|---|---|---|---|---|---|---|---|
| I-156 | J-1 | $CH_2$— | H | CH | $CH_3$ | Cl | |
| I-157 | J-1 | $CH_2$— | H | CH | $C_2H_5$ | $C_2H_5$ | |
| I-158 | J-1 | $CH_2$— | H | CH | $C_2H_5$ | $CF_3$ | |
| I-159 | J-1 | $CH_2$— | H | CH | $C_2H_5$ | $OCF_2H$ | |
| I-160 | J-1 | $CH_2$— | H | CH | $C_2H_5$ | $NHCH_3$ | |
| I-161 | J-1 | $CH_2$— | H | CH | $C_2H_5$ | Cl | |
| I-162 | J-1 | $CH_2$— | H | CH | $CF_3$ | $CF_3$ | |
| I-163 | J-1 | $CH_2$— | H | CH | $CF_3$ | $OCF_2H$ | |
| I-164 | J-1 | $CH_2$— | H | CH | $CF_3$ | $NHCH_3$ | |
| I-165 | J-1 | $CH_2$— | H | CH | $CF_3$ | $N(CH_3)_2$ | |
| I-166 | J-1 | $CH_2$— | H | CH | $CF_3$ | Cl | |
| I-167 | J-1 | $CH_2$— | H | CH | $OCF_2H$ | $OCF_2H$ | |
| I-168 | J-1 | $CH_2$— | H | CH | $OCF_2H$ | $NHCH_3$ | |
| I-169 | J-1 | $CH_2$— | H | CH | $OCF_2H$ | $N(CH_3)_2$ | |
| I-170 | J-1 | $CH_2$— | H | CH | $OCF_2H$ | Cl | |
| I-171 | J-1 | $CH_2$— | H | CH | $NHCH_3$ | $NHCH_3$ | |
| I-172 | J-1 | $CH_2$— | H | CH | $NHCH_3$ | $N(CH_3)_2$ | |
| I-173 | J-1 | $CH_2$— | H | CH | $NHCH_3$ | Cl | |
| I-174 | J-1 | $CH_2$— | H | CH | $N(CH_3)_2$ | $N(CH_3)_2$ | |
| I-175 | J-1 | $CH_2$— | H | CH | $N(CH_3)_2$ | Cl | |
| I-176 | J-1 | $CH_2$— | H | CH | Cl | Cl | |
| I-177 | J-1 | $CH_2$— | H | N | $OCH_3$ | $OCH_3$ | |
| I-178 | J-1 | $CH_2$— | H | N | $OCH_3$ | $OC_2H_5$ | |
| I-179 | J-1 | $CH_2$— | H | N | $OCH_3$ | $CH_3$ | |
| I-180 | J-1 | $CH_2$— | H | N | $OCH_3$ | $C_2H_5$ | |
| I-181 | J-1 | $CH_2$— | H | N | $OCH_3$ | $CF_3$ | |
| I-182 | J-1 | $CH_2$— | H | N | $OCH_3$ | $OCF_2H$ | |
| I-183 | J-1 | $CH_2$— | H | N | $OCH_3$ | $NHCH_3$ | |
| I-184 | J-1 | $CH_2$— | H | N | $OCH_3$ | $N(CH_3)_2$ | |
| I-185 | J-1 | $CH_2$— | H | N | $OCH_3$ | Cl | |
| I-186 | J-1 | $CH_2$— | H | N | $OC_2H_5$ | $OC_2H_5$ | |
| I-187 | J-1 | $CH_2$— | H | N | $OC_2H_5$ | $CH_3$ | |
| I-189 | J-1 | $CH_2$— | H | N | $OC_2H_5$ | $C_2H_5$ | |
| I-189 | J-1 | $CH_2$— | H | N | $OC_2H_5$ | $CF_3$ | |
| I-190 | J-1 | $CH_2$— | H | N | $OC_2H_5$ | $OCF_2H$ | |
| I-191 | J-1 | $CH_2$— | H | N | $OC_2H_5$ | $NHCH_3$ | |
| I-192 | J-1 | $CH_2$— | H | N | $OC_2H_5$ | $N(CH_3)_2$ | |
| I-193 | J-1 | $CH_2$— | H | N | $OC_2H_5$ | Cl | |
| I-194 | J-1 | $CH_2$— | H | N | $CH_3$ | $CH_3$ | |
| I-195 | J-1 | $CH_2$— | H | N | $CH_3$ | $C_2H_5$ | |
| I-196 | J-1 | $CH_2$— | H | N | $CH_3$ | $CF_3$ | |
| I-197 | J-1 | $CH_2$— | H | N | $CH_3$ | $OCF_2H$ | |
| I-198 | J-1 | $CH_2$— | H | N | $CH_3$ | $NHCH_3$ | |
| I-199 | J-1 | $CH_2$— | H | N | $CH_3$ | $N(CH_3)_2$ | |
| I-200 | J-1 | $CH_2$— | H | N | $CH_3$ | Cl | |
| I-201 | J-1 | $CH_2$— | H | N | $C_2H_5$ | $C_2H_5$ | |
| I-202 | J-1 | $CH_2$— | H | N | $C_2H_5$ | $CF_3$ | |
| I-203 | J-1 | $CH_2$— | H | N | $C_2H_5$ | $OCF_2H$ | |
| I-204 | J-1 | $CH_2$— | H | N | $C_2H_5$ | $NHCH_3$ | |
| I-205 | J-1 | $CH_2$— | H | N | $C_2H_5$ | Cl | |
| I-206 | J-1 | $CH_2$— | H | N | $CF_3$ | $CF_3$ | |
| I-207 | J-1 | $CH_2$— | H | N | $CF_3$ | $OCF_2H$ | |
| I-208 | J-1 | $CH_2$— | H | N | $CF_3$ | $NHCH_3$ | |
| I-209 | J-1 | $CH_2$— | H | N | $CF_3$ | $N(CH_3)_2$ | |
| I-210 | J-1 | $CH_2$— | H | N | $CF_3$ | Cl | |
| I-211 | J-1 | $CH_2$— | H | N | $OCF_2H$ | $OCF_2H$ | |
| I-212 | J-1 | $CH_2$— | H | N | $OCF_2H$ | $NHCH_3$ | |
| I-213 | J-1 | $CH_2$— | H | N | $OCF_2H$ | $N(CH_3)_2$ | |
| I-214 | J-1 | $CH_2$— | H | N | $OCF_2H$ | Cl | |
| I-215 | J-1 | $CH_2$— | H | N | $NHCH_3$ | $NHCH_3$ | |
| I-216 | J-1 | $CH_2$— | H | N | $NHCH_3$ | $N(CH_3)_2$ | |
| I-217 | J-1 | $CH_2$— | H | N | $NHCH_3$ | Cl | |
| I-218 | J-1 | $CH_2$— | H | N | $N(CH_3)_2$ | $N(CH_3)_2$ | |
| I-219 | J-1 | $CH_2$— | H | N | $N(CH_3)_2$ | Cl | |
| I-220 | J-1 | $CH_2$— | H | N | Cl | Cl | |
| I-221 | J-1 | $CH_2$— | $CH_3$ | N | $OCH_3$ | $OCH_3$ | |
| I-222 | J-1 | $CH_2$— | $CH_3$ | N | $OCH_3$ | $OC_2H_5$ | |
| I-223 | J-1 | $CH_2$— | $CH_3$ | N | $OCH_3$ | $CH_3$ | |
| I-224 | J-1 | $CH_2$— | $CH_3$ | N | $OCH_3$ | $C_2H_5$ | |
| I-225 | J-1 | $CH_2$— | $CH_3$ | N | $OCH_3$ | $CF_3$ | |
| I-226 | J-1 | $CH_2$— | $CH_3$ | N | $OCH_3$ | $OCF_2H$ | |
| I-227 | J-1 | $CH_2$— | $CH_3$ | N | $OCH_3$ | $NHCH_3$ | |
| I-228 | J-1 | $CH_2$— | $CH_3$ | N | $OCH_3$ | $N(CH_3)_2$ | |
| I-229 | J-1 | $CH_2$— | $CH_3$ | N | $OCH_3$ | Cl | |
| I-230 | J-1 | $CH_2$— | $CH_3$ | N | $OC_2H_5$ | $OC_2H_5$ | |
| I-231 | J-1 | $CH_2$— | $CH_3$ | N | $OC_2H_5$ | $CH_3$ | |
| I-232 | J-1 | $CH_2$— | $CH_3$ | N | $OC_2H_5$ | $C_2H_5$ | |
| I-233 | J-1 | $CH_2$— | $CH_3$ | N | $OC_2H_5$ | $CF_3$ | |
| I-234 | J-1 | $CH_2$— | $CH_3$ | N | $OC_2H_5$ | $OCF_2H$ | |
| I-235 | J-1 | $CH_2$— | $CH_3$ | N | $OC_2H_5$ | $NHCH_3$ | |
| I-236 | J-1 | $CH_2$— | $CH_3$ | N | $OC_2H_5$ | $N(CH_3)_2$ | |
| I-237 | J-1 | $CH_2$— | $CH_3$ | N | $OC_2H_5$ | Cl | |
| I-238 | J-1 | $CH_2$— | $CH_3$ | N | $CH_3$ | $CH_3$ | |
| I-239 | J-1 | $CH_2$— | $CH_3$ | N | $CH_3$ | $C_2H_5$ | |
| I-240 | J-1 | $CH_2$— | $CH_3$ | N | $CH_3$ | $CF_3$ | |
| I-241 | J-1 | $CH_2$— | $CH_3$ | N | $CH_3$ | $OCF_2H$ | |
| I-242 | J-1 | $CH_2$— | $CH_3$ | N | $CH_3$ | $NHCH_3$ | |
| I-243 | J-1 | $CH_2$— | $CH_3$ | N | $CH_3$ | $N(CH_3)_2$ | |
| I-244 | J-1 | $CH_2$— | $CH_3$ | N | $CH_3$ | Cl | |
| I-245 | J-1 | $CH_2$— | $CH_3$ | N | $C_2H_5$ | $C_2H_5$ | |
| I-246 | J-1 | $CH_2$— | $CH_3$ | N | $C_2H_5$ | $CF_3$ | |
| I-247 | J-1 | $CH_2$— | $CH_3$ | N | $C_2H_5$ | $OCF_2H$ | |
| I-248 | J-1 | $CH_2$— | $CH_3$ | N | $C_2H_5$ | $NHCH_3$ | |
| I-249 | J-1 | $CH_2$— | $CH_3$ | N | $C_2H_5$ | Cl | |
| I-250 | J-1 | $CH_2$— | $CH_3$ | N | $CF_3$ | $CF_3$ | |
| I-251 | J-1 | $CH_2$— | $CH_3$ | N | $CF_3$ | $OCF_2H$ | |
| I-252 | J-1 | $CH_2$— | $CH_3$ | N | $CF_3$ | $NHCH_3$ | |
| I-253 | J-1 | $CH_2$— | $CH_3$ | N | $CF_3$ | $N(CH_3)_2$ | |
| I-254 | J-1 | $CH_2$— | $CH_3$ | N | $CF_3$ | Cl | |
| I-255 | J-1 | $CH_2$— | $CH_3$ | N | $OCF_2H$ | $OCF_2H$ | |
| I-256 | J-1 | $CH_2$— | $CH_3$ | N | $OCF_2H$ | $NHCH_3$ | |
| I-257 | J-1 | $CH_2$— | $CH_3$ | N | $OCF_2H$ | $N(CH_3)_2$ | |
| I-258 | J-1 | $CH_2$— | $CH_3$ | N | $OCF_2H$ | Cl | |
| I-259 | J-1 | $CH_2$— | $CH_3$ | N | $NHCH_3$ | $NHCH_3$ | |
| I-260 | J-1 | $CH_2$— | $CH_3$ | N | $NHCH_3$ | $N(CH_3)_2$ | |
| I-261 | J-1 | $CH_2$— | $CH_3$ | N | $NHCH_3$ | Cl | |
| I-262 | J-1 | $CH_2$— | $CH_3$ | N | $N(CH_3)_2$ | $N(CH_3)_2$ | |
| I-263 | J-1 | $CH_2$— | $CH_3$ | N | $N(CH_3)_2$ | Cl | |
| I-264 | J-1 | $CH_2$— | $CH_3$ | N | Cl | Cl | |
| I-265 | J-2 | — | H | CH | $OCH_3$ | $OCH_3$ | 167–168 171–172(+) |
| I-266 | J-2 | — | H | CH | $OCH_3$ | $OC_2H_5$ | 154 |
| I-267 | J-2 | — | H | CH | $OCH_3$ | $CH_3$ | 180–181(+) |
| I-268 | J-2 | — | H | CH | $OCH_3$ | $C_2H_5$ | |
| I-269 | J-2 | — | H | CH | $OCH_3$ | $CF_3$ | |
| I-270 | J-2 | — | H | CH | $OCH_3$ | $OCF_2H$ | |
| I-271 | J-2 | — | H | CH | $OCH_3$ | $NHCH_3$ | |
| I-272 | J-2 | — | H | CH | $OCH_3$ | $N(CH_3)_2$ | 199,5 |
| I-273 | J-2 | — | H | CH | $OCH_3$ | Cl | 110–111 175–178(+) |
| I-274 | J-2 | — | H | CH | $OC_2H_5$ | $OC_2H_5$ | 152–154(+) |
| I-275 | J-2 | — | H | CH | $OC_2H_5$ | $CH_3$ | |
| I-276 | J-2 | — | H | CH | $OC_2H_5$ | $C_2H_5$ | |
| I-277 | J-2 | — | H | CH | $OC_2H_5$ | $CF_3$ | |
| I-278 | J-2 | — | H | CH | $OC_2H_5$ | $OCF_2H$ | |
| I-279 | J-2 | — | H | CH | $OC_2H_5$ | $NHCH_3$ | |
| I-280 | J-2 | — | H | CH | $OC_2H_5$ | $N(CH_3)_2$ | |
| I-281 | J-2 | — | H | CH | $OC_2H_5$ | Cl | 158–159 213(+) |
| I-282 | J-2 | — | H | CH | $CH_3$ | $CH_3$ | 153 |
| I-283 | J-2 | — | H | CH | $CH_3$ | $C_2H_5$ | |
| I-284 | J-2 | — | H | CH | $CH_3$ | $CF_3$ | |
| I-285 | J-2 | — | H | CH | $CH_3$ | $OCF_2H$ | |
| I-286 | J-2 | — | H | CH | $CH_3$ | $NHCH_3$ | |
| I-287 | J-2 | — | H | CH | $CH_3$ | $N(CH_3)_2$ | |
| I-288 | J-2 | — | H | CH | $CH_3$ | Cl | 109–109 >300(+) |
| I-289 | J-2 | — | H | CH | $C_2H_5$ | $C_2H_5$ | |
| I-290 | J-2 | — | H | CH | $C_2H_5$ | $CF_3$ | |
| I-291 | J-2 | — | H | CH | $C_2H_5$ | $OCF_2H$ | |
| I-292 | J-2 | — | H | CH | $C_2H_5$ | $NHCH_3$ | |
| I-293 | J-2 | — | H | CH | $C_2H_5$ | Cl | |
| I-294 | J-2 | — | H | CH | $CF_3$ | $CF_3$ | |
| I-295 | J-2 | — | H | CH | $CF_3$ | $OCF_2H$ | |
| I-296 | J-2 | — | H | CH | $CF_3$ | $NHCH_3$ | |
| I-297 | J-2 | — | H | CH | $CF_3$ | $N(CH_3)_2$ | |

TABLE 1-continued

Examples of compounds of the formula (I) having
$R^4 = R^5 = R^6 = R^7 = H$ and $CH_3$; and $R^{10} = H$:

| Ex. No. | J | E | $R^1$ | A | $R^2$ | $R^3$ | m.p. (°C.) |
|---|---|---|---|---|---|---|---|
| I-298 | J-2 | — | H | CH | $CF_3$ | Cl | |
| I-299 | J-2 | — | H | CH | $OCF_2H$ | $OCF_2H$ | |
| I-300 | J-2 | — | H | CH | $OCF_2H$ | $NHCH_3$ | |
| I-301 | J-2 | — | H | CH | $OCF_2H$ | $N(CH_3)_2$ | |
| I-302 | J-2 | — | H | CH | $OCF_2H$ | Cl | |
| I-303 | J-2 | — | H | CH | $NHCH_3$ | $NHCH_3$ | |
| I-304 | J-2 | — | H | CH | $NHCH_3$ | $N(CH_3)_2$ | |
| I-305 | J-2 | — | H | CH | $NHCH_3$ | Cl | |
| I-306 | J-2 | — | H | CH | $N(CH_3)_2$ | $N(CH_3)_2$ | |
| I-307 | J-2 | — | H | CH | $N(CH_3)_2$ | Cl | |
| I-308 | J-2 | — | H | CH | Cl | Cl | |
| I-309 | J-2 | — | H | N | $OCH_3$ | $OCH_3$ | 255 159–162$^{(+)}$ |
| I-310 | J-2 | — | H | N | $OCH_3$ | $OC_2H_5$ | |
| I-311 | J-2 | — | H | N | $OCH_3$ | $CH_3$ | |
| I-312 | J-2 | — | H | N | $OCH_3$ | $C_2H_5$ | |
| I-313 | J-2 | — | H | N | $OCH_3$ | $CF_3$ | |
| I-314 | J-2 | — | H | N | $OCH_3$ | $OCF_2H$ | |
| I-315 | J-2 | — | H | N | $OCH_3$ | $NHCH_3$ | |
| I-316 | J-2 | — | H | N | $OCH_3$ | $N(CH_3)_2$ | 156$^{(+)}$ |
| I-317 | J-2 | — | H | N | $OCH_3$ | Cl | |
| I-318 | J-2 | — | H | N | $OC_2H_5$ | $OC_2H_5$ | |
| I-319 | J-2 | — | H | N | $OC_2H_5$ | $CH_3$ | |
| I-320 | J-2 | — | H | N | $OC_2H_5$ | $C_2H_5$ | |
| I-321 | J-2 | — | H | N | $OC_2H_5$ | $CF_3$ | |
| I-322 | J-2 | — | H | N | $OC_2H_5$ | $OCF_2H$ | |
| I-323 | J-2 | — | H | N | $OC_2H_5$ | $NHCH_3$ | |
| I-324 | J-2 | — | H | N | $OC_2H_5$ | $N(CH_3)_2$ | |
| I-325 | J-2 | — | H | N | $OC_2H_5$ | Cl | 213$^{(+)}$ |
| I-326 | J-2 | — | H | N | $CH_3$ | $CH_3$ | |
| I-327 | J-2 | — | H | N | $CH_3$ | $C_2H_5$ | |
| I-328 | J-2 | — | H | N | $CH_3$ | $CF_3$ | |
| I-329 | J-2 | — | H | N | $CH_3$ | $OCF_2H$ | |
| I-330 | J-2 | — | H | N | $CH_3$ | $NHCH_3$ | |
| I-331 | J-2 | — | H | N | $CH_3$ | $N(CH_3)_2$ | |
| I-332 | J-2 | — | H | N | $CH_3$ | Cl | |
| I-333 | J-2 | — | H | N | $C_2H_5$ | $C_2H_5$ | |
| I-334 | J-2 | — | H | N | $C_2H_5$ | $CF_3$ | |
| I-335 | J-2 | — | H | N | $C_2H_5$ | $OCF_2H$ | |
| I-336 | J-2 | — | H | N | $C_2H_5$ | $NHCH_3$ | |
| I-337 | J-2 | — | H | N | $C_2H_5$ | Cl | |
| I-338 | J-2 | — | H | N | $CF_3$ | $CF_3$ | |
| I-339 | J-2 | — | H | N | $CF_3$ | $OCF_2H$ | |
| I-340 | J-2 | — | H | N | $CF_3$ | $NHCH_3$ | |
| I-341 | J-2 | — | H | N | $CF_3$ | $N(CH_3)_2$ | |
| I-342 | J-2 | — | H | N | $CF_3$ | Cl | |
| I-343 | J-2 | — | H | N | $OCF_2H$ | $OCF_2H$ | |
| I-344 | J-2 | — | H | N | $OCF_2H$ | $NHCH_3$ | |
| I-345 | J-2 | — | H | N | $OCF_2H$ | $N(CH_3)_2$ | |
| I-346 | J-2 | — | H | N | $OCF_2H$ | Cl | |
| I-347 | J-2 | — | H | N | $NHCH_3$ | $NHCH_3$ | |
| I-348 | J-2 | — | H | N | $NHCH_3$ | $N(CH_3)_2$ | |
| I-349 | J-2 | — | H | N | $NHCH_3$ | Cl | |
| I-350 | J-2 | — | H | N | $N(CH_3)_2$ | $N(CH_3)_2$ | |
| I-351 | J-2 | — | H | N | $N(CH_3)_2$ | Cl | |
| I-352 | J-2 | — | H | N | Cl | Cl | |
| I-353 | J-2 | — | $CH_3$ | N | $OCH_3$ | $OCH_3$ | |
| I-354 | J-2 | — | $CH_3$ | N | $OCH_3$ | $OC_2H_5$ | |
| I-355 | J-2 | — | $CH_3$ | N | $OCH_3$ | $CH_3$ | |
| I-356 | J-2 | — | $CH_3$ | N | $OCH_3$ | $C_2H_5$ | |
| I-357 | J-2 | — | $CH_3$ | N | $OCH_3$ | $CF_3$ | |
| I-358 | J-2 | — | $CH_3$ | N | $OCH_3$ | $OCF_2H$ | |
| I-359 | J-2 | — | $CH_3$ | N | $OCH_3$ | $NHCH_3$ | |
| I-360 | J-2 | — | $CH_3$ | N | $OCH_3$ | $N(CH_3)_2$ | |
| I-361 | J-2 | — | $CH_3$ | N | $OCH_3$ | Cl | |
| I-362 | J-2 | — | $CH_3$ | N | $OC_2H_5$ | $OC_2H_5$ | |
| I-363 | J-2 | — | $CH_3$ | N | $OC_2H_5$ | $CH_3$ | |
| I-364 | J-2 | — | $CH_3$ | N | $OC_2H_5$ | $C_2H_5$ | |
| I-365 | J-2 | — | $CH_3$ | N | $OC_2H_5$ | $CF_3$ | |
| I-366 | J-2 | — | $CH_3$ | N | $OC_2H_5$ | $OCF_2H$ | |
| I-367 | J-2 | — | $CH_3$ | N | $OC_2H_5$ | $NHCH_3$ | |
| I-368 | J-2 | — | $CH_3$ | N | $OC_2H_5$ | $N(CH_3)_2$ | |
| I-369 | J-2 | — | $CH_3$ | N | $OC_2H_5$ | Cl | |
| I-370 | J-2 | — | $CH_3$ | N | $CH_3$ | $CH_3$ | |
| I-371 | J-2 | — | $CH_3$ | N | $CH_3$ | $C_2H_5$ | |
| I-372 | J-2 | — | $CH_3$ | N | $CH_3$ | $CF_3$ | |
| I-373 | J-2 | — | $CH_3$ | N | $CH_3$ | $OCF_2H$ | |
| I-374 | J-2 | — | $CH_3$ | N | $CH_3$ | $NHCH_3$ | |
| I-375 | J-2 | — | $CH_3$ | N | $CH_3$ | $N(CH_3)_2$ | |
| I-376 | J-2 | — | $CH_3$ | N | $CH_3$ | Cl | |
| I-377 | J-2 | — | $CH_3$ | N | $C_2H_2$ | $C_2H_5$ | |
| I-378 | J-2 | — | $CH_3$ | N | $C_2H_5$ | $CF_3$ | |
| I-379 | J-2 | — | $CH_3$ | N | $C_2H_5$ | $OCF_2H$ | |
| I-380 | J-2 | — | $CH_3$ | N | $C_2H_5$ | $NHCH_3$ | |
| I-381 | J-2 | — | $CH_3$ | N | $C_2H_5$ | Cl | |
| I-382 | J-2 | — | $CH_3$ | N | $CF_3$ | $CF_3$ | |
| I-383 | J-2 | — | $CH_3$ | N | $CF_3$ | $OCF_2H$ | |
| I-384 | J-2 | — | $CH_3$ | N | $CF_3$ | $NHCH_3$ | |
| I-385 | J-2 | — | $CH_3$ | N | $CF_3$ | $N(CH_3)_2$ | |
| I-386 | J-2 | — | $CH_3$ | N | $CF_3$ | Cl | |
| I-387 | J-2 | — | $CH_3$ | N | $OCF_2H$ | $OCF_2H$ | |
| I-388 | J-2 | — | $CH_3$ | N | $OCF_2H$ | $NHCH_3$ | |
| I-389 | J-2 | — | $CH_3$ | N | $OCF_2H$ | $N(CH_3)_2$ | |
| I-390 | J-2 | — | $CH_3$ | N | $OCF_2H$ | Cl | |
| I-391 | J-2 | — | $CH_3$ | N | $NHCH_3$ | $NHCH_3$ | |
| I-392 | J-2 | — | $CH_3$ | N | $NHCH_3$ | $N(CH_3)_2$ | |
| I-393 | J-2 | — | $CH_3$ | N | $NHCH_3$ | Cl | |
| I-394 | J-2 | — | $CH_3$ | N | $N(CH_3)_2$ | $N(CH_3)_2$ | |
| I-395 | J-2 | — | $CH_3$ | N | $N(CH_3)_2$ | Cl | |
| I-396 | J-2 | — | $CH_3$ | N | Cl | Cl | |
| I-397 | J-3 | — | H | CH | $OCH_3$ | $OCH_3$ | 250 (d.)$^{(+)}$ |
| I-398 | J-3 | — | H | CH | $OCH_3$ | $OC_2H_5$ | |
| I-399 | J-3 | — | H | CH | $OCH_3$ | $CH_3$ | |
| I-400 | J-3 | — | H | CH | $OCH_3$ | $C_2H_5$ | |
| I-401 | J-3 | — | H | CH | $OCH_3$ | $CF_3$ | |
| I-402 | J-3 | — | H | CH | $OCH_3$ | $OCF_2H$ | |
| I-403 | J-3 | — | H | CH | $OCH_3$ | $NHCH_3$ | |
| I-404 | J-3 | — | H | CH | $OCH_3$ | $N(CH_3)_2$ | |
| I-405 | J-3 | — | H | CH | $OCH_3$ | Cl | |
| I-406 | J-3 | — | H | CH | $OC_2H_5$ | $OC_2H_5$ | |
| I-407 | J-3 | — | H | CH | $OC_2H_5$ | $CH_3$ | |
| I-408 | J-3 | — | H | CH | $OC_2H_5$ | $C_2H_5$ | |
| I-409 | J-3 | — | H | CH | $OC_2H_5$ | $CF_3$ | |
| I-410 | J-3 | — | H | CH | $OC_2H_5$ | $OCF_2H$ | |
| I-411 | J-3 | — | H | CH | $OC_2H_5$ | $NHCH_3$ | |
| I-412 | J-3 | — | H | CH | $OC_2H_5$ | $N(CH_3)_2$ | |
| I-413 | J-3 | — | H | CH | $OC_2H_5$ | Cl | |
| I-414 | J-3 | — | H | CH | $CH_3$ | $CH_3$ | 180–2 |
| I-415 | J-3 | — | H | CH | $CH_3$ | $C_2H_5$ | |
| I-416 | J-3 | — | H | CH | $CH_3$ | $CF_3$ | |
| I-417 | J-3 | — | H | CH | $CH_3$ | $OCF_2H$ | |
| I-418 | J-3 | — | H | CH | $CH_3$ | $NHCH_3$ | |
| I-419 | J-3 | — | H | CH | $CH_3$ | $N(CH_3)_2$ | |
| I-420 | J-3 | — | H | CH | $CH_3$ | Cl | |
| I-421 | J-3 | — | H | CH | $C_2H_5$ | $C_2H_5$ | |
| I-422 | J-3 | — | H | CH | $C_2H_5$ | $CF_3$ | |
| I-423 | J-3 | — | H | CH | $C_2H_5$ | $OCF_2H$ | |
| I-424 | J-3 | — | H | CH | $C_2H_5$ | $NHCH_3$ | |
| I-425 | J-3 | — | H | CH | $C_2H_5$ | Cl | |
| I-426 | J-3 | — | H | CH | $CF_3$ | $CF_3$ | |
| I-427 | J-3 | — | H | CH | $CF_3$ | $OCF_2H$ | |
| I-428 | J-3 | — | H | CH | $CF_3$ | $NHCH_3$ | |
| I-429 | J-3 | — | H | CH | $CF_3$ | $N(CH_3)_2$ | |
| I-430 | J-3 | — | H | CH | $CF_3$ | Cl | |
| I-431 | J-3 | — | H | CH | $OCF_2H$ | $OCF_2H$ | |
| I-432 | J-3 | — | H | CH | $OCF_2H$ | $NHCH_3$ | |
| I-433 | J-3 | — | H | CH | $OCF_2H$ | $N(CH_3)_2$ | |
| I-434 | J-3 | — | H | CH | $OCF_2H$ | Cl | |
| I-435 | J-3 | — | H | CH | $NHCH_3$ | $NHCH_3$ | |
| I-436 | J-3 | — | H | CH | $NHCH_3$ | $N(CH_3)_2$ | |
| I-437 | J-3 | — | H | CH | $NHCH_3$ | Cl | |
| I-438 | J-3 | — | H | CH | $N(CH_3)_2$ | $N(CH_3)_2$ | |
| I-439 | J-3 | — | H | CH | $N(CH_3)_2$ | Cl | |
| I-440 | J-3 | — | H | CH | Cl | Cl | |
| I-441 | J-3 | — | H | N | $OCH_3$ | $OCH_3$ | 169–72 |

TABLE 1-continued

Examples of compounds of the formula (I) having
$R^4 = R^5 = R^6 = R^7 = H$ and $CH_3$: and $R^{10} = H$:

| Ex. No. | J | E | $R^1$ | A | $R^2$ | $R^3$ | m.p. (°C.) |
|---|---|---|---|---|---|---|---|
| I-442 | J-3 | — | H | N | $OCH_3$ | $OC_2H_5$ | (d.) |
| I-443 | J-3 | — | H | N | $OCH_3$ | $CH_3$ | 190–2$^{(+)}$ |
| I-444 | J-3 | — | H | N | $OCH_3$ | $C_2H_5$ | |
| I-445 | J-3 | — | H | N | $OCH_3$ | $CF_3$ | |
| I-446 | J-3 | — | H | N | $OCH_3$ | $OCF_2H$ | |
| I-447 | J-3 | — | H | N | $OCH_3$ | $NHCH_3$ | |
| I-448 | J-3 | — | H | N | $OCH_3$ | $N(CH_3)_2$ | |
| I-449 | J-3 | — | H | N | $OCH_3$ | Cl | |
| I-450 | J-3 | — | H | N | $OC_2H_5$ | $OC_2H_5$ | |
| I-451 | J-3 | — | H | N | $OC_2H_5$ | $CH_3$ | |
| I-452 | J-3 | — | H | N | $OC_2H_5$ | $C_2H_5$ | |
| I-453 | J-3 | — | H | N | $OC_2H_5$ | $CF_3$ | |
| I-454 | J-3 | — | H | N | $OC_2H_5$ | $OCF_2H$ | |
| I-455 | J-3 | — | H | N | $OC_2H_5$ | $NHCH_3$ | |
| I-456 | J-3 | — | H | N | $OC_2H_5$ | $N(CH_3)_2$ | |
| I-457 | J-3 | — | H | N | $OC_2H_5$ | Cl | |
| I-458 | J-3 | — | H | N | $CH_3$ | $CH_3$ | |
| I-459 | J-3 | — | H | N | $CH_3$ | $C_2H_5$ | |
| I-460 | J-3 | — | H | N | $CH_3$ | $CF_3$ | |
| I-461 | J-3 | — | H | N | $CH_3$ | $OCF_2H$ | |
| I-462 | J-3 | — | H | N | $CH_3$ | $NHCH_3$ | |
| I-463 | J-3 | — | H | N | $CH_3$ | $N(CH_3)_2$ | |
| I-464 | J-3 | — | H | N | $CH_3$ | Cl | |
| I-465 | J-3 | — | H | N | $C_2H_5$ | $C_2H_5$ | |
| I-466 | J-3 | — | H | N | $C_2H_5$ | $CF_3$ | |
| I-467 | J-3 | — | H | N | $C_2H_5$ | $OCF_2H$ | |
| I-468 | J-3 | — | H | N | $C_2H_5$ | $NHCH_3$ | |
| I-469 | J-3 | — | H | N | $C_2H_5$ | Cl | |
| I-470 | J-3 | — | H | N | $CF_3$ | $CF_3$ | |
| I-471 | J-3 | — | H | N | $CF_3$ | $OCF_2H$ | |
| I-472 | J-3 | — | H | N | $CF_3$ | $NHCH_3$ | |
| I-473 | J-3 | — | H | N | $CF_3$ | $N(CH_3)_2$ | |
| I-474 | J-3 | — | H | N | $CF_3$ | Cl | |
| I-475 | J-3 | — | H | N | $OCF_2H$ | $OCF_2H$ | |
| I-476 | J-3 | — | H | N | $OCF_2H$ | $NHCH_3$ | |
| I-477 | J-3 | — | H | N | $OCF_2H$ | $N(CH_3)_2$ | |
| I-478 | J-3 | — | H | N | $OCF_2H$ | Cl | |
| I-479 | J-3 | — | H | N | $NHCH_3$ | $NHCH_3$ | |
| I-480 | J-3 | — | H | N | $NHCH_3$ | $N(CH_3)_2$ | |
| I-481 | J-3 | — | H | N | $NHCH_3$ | Cl | |
| I-482 | J-3 | — | H | N | $N(CH_3)_2$ | $N(CH_3)_2$ | |
| I-483 | J-3 | — | H | N | $N(CH_3)_2$ | Cl | |
| I-484 | J-3 | — | H | N | Cl | Cl | |
| I-485 | J-3 | — | $CH_3$ | N | $OCH_3$ | $OCH_3$ | 204 (de-comp.) |
| I-486 | J-3 | — | $CH_3$ | N | $OCH_3$ | $OC_2H_5$ | |
| I-487 | J-3 | — | $CH_3$ | N | $OCH_3$ | $CH_3$ | |
| I-488 | J-3 | — | $CH_3$ | N | $OCH_3$ | $C_2H_5$ | |
| I-489 | J-3 | — | $CH_3$ | N | $OCH_3$ | $CF_3$ | |
| I-490 | J-3 | — | $CH_3$ | N | $OCH_3$ | $OCF_2H$ | |
| I-491 | J-3 | — | $CH_3$ | N | $OCH_3$ | $NHCH_3$ | |
| I-492 | J-3 | — | $CH_3$ | N | $OCH_3$ | $N(CH_3)_2$ | |
| I-493 | J-3 | — | $CH_3$ | N | $OCH_3$ | Cl | |
| I-494 | J-3 | — | $CH_3$ | N | $OC_2H_5$ | $OC_2H_5$ | |
| I-495 | J-3 | — | $CH_3$ | N | $OC_2H_5$ | $CH_3$ | |
| I-496 | J-3 | — | $CH_3$ | N | $OC_2H_5$ | $C_2H_5$ | |
| I-497 | J-3 | — | $CH_3$ | N | $OC_2H_5$ | $CF_3$ | |
| I-498 | J-3 | — | $CH_3$ | N | $OC_2H_5$ | $OCF_2H$ | |
| I-499 | J-3 | — | $CH_3$ | N | $OC_2H_5$ | $NHCH_3$ | |
| I-500 | J-3 | — | $CH_3$ | N | $OC_2H_5$ | $N(CH_3)_2$ | |
| I-501 | J-3 | — | $CH_3$ | N | $OC_2H_5$ | Cl | |
| I-502 | J-3 | — | $CH_3$ | N | $CH_3$ | $CH_3$ | |
| I-503 | J-3 | — | $CH_3$ | N | $CH_3$ | $C_2H_5$ | |
| I-504 | J-3 | — | $CH_3$ | N | $CH_3$ | $CF_3$ | |
| I-505 | J-3 | — | $CH_3$ | N | $CH_3$ | $OCF_2H$ | |
| I-506 | J-3 | — | $CH_3$ | N | $CH_3$ | $NHCH_3$ | |
| I-507 | J-3 | — | $CH_3$ | N | $CH_3$ | $N(CH_3)_2$ | |
| I-508 | J-3 | — | $CH_3$ | N | $CH_3$ | Cl | |
| I-509 | J-3 | — | $CH_3$ | N | $C_2H_5$ | $C_2H_5$ | |
| I-510 | J-3 | — | $CH_3$ | N | $C_2H_5$ | $CF_3$ | |
| I-511 | J-3 | — | $CH_3$ | N | $C_2H_5$ | $OCF_2H$ | |
| I-512 | J-3 | — | $CH_3$ | N | $C_2H_5$ | $NHCH_3$ | |
| I-513 | J-3 | — | $CH_3$ | N | $C_2H_5$ | Cl | |
| I-514 | J-3 | — | $CH_3$ | N | $CF_3$ | $CF_3$ | |
| I-515 | J-3 | — | $CH_3$ | N | $CF_3$ | $OCF_2H$ | |
| I-516 | J-3 | — | $CH_3$ | N | $CF_3$ | $NHCH_3$ | |
| I-517 | J-3 | — | $CH_3$ | N | $CF_3$ | $N(CH_3)_2$ | |
| I-518 | J-3 | — | $CH_3$ | N | $CF_3$ | Cl | |
| I-519 | J-3 | — | $CH_3$ | N | $OCF_2H$ | $OCF_2H$ | |
| I-520 | J-3 | — | $CH_3$ | N | $OCF_2H$ | $NHCH_3$ | |
| I-521 | J-3 | — | $CH_3$ | N | $OCF_2H$ | $N(CH_3)_2$ | |
| I-522 | J-3 | — | $CH_3$ | N | $OCF_2H$ | Cl | |
| I-523 | J-3 | — | $CH_3$ | N | $NHCH_3$ | $NHCH_3$ | |
| I-524 | J-3 | — | $CH_3$ | N | $NHCH_3$ | $N(CH_3)_2$ | |
| I-525 | J-3 | — | $CH_3$ | N | $NHCH_3$ | Cl | |
| I-526 | J-3 | — | $CH_3$ | N | $N(CH_3)_2$ | $N(CH_3)_2$ | |
| I-527 | J-3 | — | $CH_3$ | N | $N(CH_3)_2$ | Cl | |
| I-528 | J-3 | — | $CH_3$ | N | Cl | Cl | |
| I-529 | J-4 | — | H | CH | $OCH_3$ | $OCH_3$ | 185–186 151–152$^{(+)}$ |
| I-530 | J-4 | — | H | CH | $OCH_3$ | $OC_2H_5$ | 174–175 85$^{(+)}$ |
| I-531 | J-4 | — | H | CH | $OCH_3$ | $CH_3$ | 178 165–167$^{(+)}$ |
| I-532 | J-4 | — | H | CH | $OCH_3$ | $C_2H_5$ | |
| I-533 | J-4 | — | H | CH | $OCH3$ | $CF_3$ | |
| I-534 | J-4 | — | H | CH | $OCH_3$ | $OCF_2H$ | |
| I-535 | J-4 | — | H | CH | $OCH_3$ | $NHCH_3$ | |
| I-536 | J-4 | — | H | CH | $OCH_3$ | $N(CH_3)_2$ | 92–95 258–262$^{(+)}$ |
| I-537 | J-4 | — | H | CH | $OCH_3$ | Cl | 112 185–186 |
| I-538 | J-4 | — | H | CH | $OC_2H_5$ | $OC_2H_5$ | 134–137 |
| I-539 | J-4 | — | H | CH | $OC_2H_5$ | $CH_3$ | |
| I-540 | J-4 | — | H | CH | $OC_2H_5$ | $C_2H_5$ | |
| I-541 | J-4 | — | H | CH | $OC_2H_5$ | $CF_3$ | |
| I-542 | J-4 | — | H | CH | $OC_2H_5$ | $OCF_2H$ | |
| I-543 | J-4 | — | H | CH | $OC_2H_5$ | $NHCH_3$ | |
| I-544 | J-4 | — | H | CH | $OC_2H_5$ | $N(CH_3)_2$ | |
| I-545 | J-4 | — | H | CH | $OC_2H_5$ | Cl | 181–183 171$^{(+)}$ |
| I-546 | J-4 | — | H | CH | $CH_3$ | $CH_3$ | 195 230–232$^{(+)}$ |
| I-547 | J-4 | — | H | CH | $CH_3$ | $C_2H_5$ | |
| I-548 | J-4 | — | H | CH | $CH_3$ | $CF_3$ | |
| I-549 | J-4 | — | H | CH | $CH_3$ | $OCF_2H$ | |
| I-550 | J-4 | — | H | CH | $CH_3$ | $NHCH_3$ | |
| I-551 | J-4 | — | H | CH | $CH_3$ | $N(CH_3)_2$ | |
| I-552 | J-4 | — | H | CH | $CH_3$ | Cl | 175 138–140$^{(+)}$ |
| I-553 | J-4 | — | H | CH | $C_2H_5$ | $C_2H_5$ | |
| I-554 | J-4 | — | H | CH | $C_2H_5$ | $CF_3$ | |
| I-555 | J-4 | — | H | CH | $C_2H_5$ | $OCF_2H$ | |
| I-556 | J-4 | — | H | CH | $C_2H_5$ | $NHCH_3$ | |
| I-557 | J-4 | — | H | CH | $C_2H_5$ | Cl | |
| I-558 | J-4 | — | H | CH | $CF_3$ | $CF_3$ | |
| I-559 | J-4 | — | H | CH | $CF_3$ | $OCF_2H$ | |
| I-560 | J-4 | — | H | CH | $CF_3$ | $NHCH_3$ | |
| I-561 | J-4 | — | H | CH | $CF_3$ | $N(CH_3)_2$ | |
| I-562 | J-4 | — | H | CH | $CF_3$ | Cl | |
| I-563 | J-4 | — | H | CH | $OCF_2H$ | $OCF_2H$ | |
| I-564 | J-4 | — | H | CH | $OCF_2H$ | $NHCH_3$ | |
| I-565 | J-4 | — | H | CH | $OCF_2H$ | $N(CH_3)_2$ | |
| I-566 | J-4 | — | H | CH | $OCF_2H$ | Cl | |
| I-567 | J-4 | — | H | CH | $NHCH_3$ | $NHCH_3$ | |
| I-568 | J-4 | — | H | CH | $NHCH_3$ | $N(CH_3)_2$ | |
| I-569 | J-4 | — | H | CH | $NHCH_3$ | Cl | |
| I-570 | J-4 | — | H | CH | $N(CH_3)_2$ | $N(CH_3)_2$ | |
| I-571 | J-4 | — | H | CH | $N(CH_3)_2$ | Cl | |
| I-572 | J-4 | — | H | CH | Cl | Cl | |
| I-573 | J-4 | — | H | N | $OCH_3$ | $OCH_3$ | 179 |
| I-574 | J-4 | — | H | N | $OCH_3$ | $OC_2H_5$ | |
| I-575 | J-4 | — | H | N | $OCH_3$ | $CH_3$ | 238$^{(+)}$ |

TABLE 1-continued

Examples of compounds of the formula (I) having
$R^4 = R^5 = R^6 = R^7 = H$ and $CH_3$; and $R^{10} = H$:

| Ex. No. | J | E | $R^1$ | A | $R^2$ | $R^3$ | m.p. (°C.) |
|---|---|---|---|---|---|---|---|
| I-576 | J-4 | — | H | N | $OCH_3$ | $C_2H_5$ | |
| I-577 | J-4 | — | H | N | $OCH_3$ | $CF_3$ | |
| I-578 | J-4 | — | H | N | $OCH_3$ | $OCF_2H$ | |
| I-579 | J-4 | — | H | N | $OCH_3$ | $NHCH_3$ | |
| I-580 | J-4 | — | H | N | $OCH_3$ | $N(CH_3)_2$ | |
| I-581 | J-4 | — | H | N | $OCH_3$ | Cl | |
| I-582 | J-4 | — | H | N | $OC_2H_5$ | $OC_2H_5$ | |
| I-583 | J-4 | — | H | N | $OC_2H_5$ | $CH_3$ | |
| I-584 | J-4 | — | H | N | $OC_2H_5$ | $C_2H_5$ | |
| I-585 | J-4 | — | H | N | $OC_2H_5$ | $CF_3$ | |
| I-586 | J-4 | — | H | N | $OC_2H_5$ | $OCF_2H$ | |
| I-587 | J-4 | — | H | N | $OC_2H_5$ | $NHCH_3$ | |
| I-588 | J-4 | — | H | N | $OC_2H_5$ | $N(CH_3)_2$ | |
| I-589 | J-4 | — | H | N | $OC_2H_5$ | Cl | |
| I-590 | J-4 | — | H | N | $CH_3$ | $CH_3$ | 200 177–178(+) |
| I-591 | J-4 | — | H | N | $CH_3$ | $C_2H_5$ | |
| I-592 | J-4 | — | H | N | $CH_3$ | $CF_3$ | |
| I-593 | J-4 | — | H | N | $CH_3$ | $OCF_2H$ | |
| I-594 | J-4 | — | H | N | $CH_3$ | $NHCH_3$ | |
| I-595 | J-4 | — | H | N | $CH_3$ | $N(CH_3)_2$ | |
| I-596 | J-4 | — | H | N | $CH_3$ | Cl | |
| I-597 | J-4 | — | H | N | $C_2H_5$ | $C_2H_5$ | |
| I-598 | J-4 | — | H | N | $C_2H_5$ | $CF_3$ | |
| I-599 | J-4 | — | H | N | $C_2H_5$ | $OCF_2H$ | |
| I-600 | J-4 | — | H | N | $C_2H_5$ | $NHCH_3$ | |
| I-601 | J-4 | — | H | N | $C_2H_5$ | Cl | |
| I-602 | J-4 | — | H | N | $CF_3$ | $CF_3$ | |
| I-603 | J-4 | — | H | N | $CF_3$ | $OCF_2H$ | |
| I-604 | J-4 | — | H | N | $CF_3$ | $NHCH_3$ | |
| I-605 | J-4 | — | H | N | $CF_3$ | $N(CH_3)_2$ | |
| I-606 | J-4 | — | H | N | $CF_3$ | Cl | |
| I-607 | J-4 | — | H | N | $OCF_2H$ | $OCF_2H$ | |
| I-608 | J-4 | — | H | N | $OCF_2H$ | $NHCH_3$ | |
| I-609 | J-4 | — | H | N | $OCF_2H$ | $N(CH_3)_2$ | |
| I-610 | J-4 | — | H | N | $OCF_2H$ | Cl | |
| I-611 | J-4 | — | H | N | $NHCH_3$ | $NHCH_3$ | |
| I-612 | J-4 | — | H | N | $NHCH_3$ | $N(CH_3)_2$ | |
| I-613 | J-4 | — | H | N | $NHCH_3$ | Cl | |
| I-614 | J-4 | — | H | N | $N(CH_3)_2$ | $N(CH_3)_2$ | |
| I-615 | J-4 | — | H | N | $N(CH_3)_2$ | Cl | |
| I-616 | J-4 | — | H | N | Cl | Cl | |
| I-617 | J-4 | — | $CH_3$ | N | $OCH_3$ | $OCH_3$ | 97–100(+) |
| I-618 | J-4 | — | $CH_3$ | N | $OCH_3$ | $OC_2H_5$ | |
| I-619 | J-4 | — | $CH_3$ | N | $OCH_3$ | $CH_3$ | |
| I-620 | J-4 | — | $CH_3$ | N | $OCH_3$ | $C_2H_5$ | |
| I-621 | J-4 | — | $CH_3$ | N | $OCH_3$ | $CF_3$ | |
| I-622 | J-4 | — | $CH_3$ | N | $OCH_3$ | $OCF_2H$ | |
| I-623 | J-4 | — | $CH_3$ | N | $OCH_3$ | $NHCH_3$ | |
| I-624 | J-4 | — | $CH_3$ | N | $OCH_3$ | $N(CH_3)_2$ | |
| I-625 | J-4 | — | $CH_3$ | N | $OCH_3$ | Cl | |
| I-626 | J-4 | — | $CH_3$ | N | $OC_2H_5$ | $OC_2H_5$ | |
| I-627 | J-4 | — | $CH_3$ | N | $OC_2H_5$ | $CH_3$ | |
| I-628 | J-4 | — | $CH_3$ | N | $OC_2H_5$ | $C_2H_5$ | |
| I-629 | J-4 | — | $CH_3$ | N | $OC_2H_5$ | $CF_3$ | |
| I-630 | J-4 | — | $CH_3$ | N | $OC_2H_5$ | $OCF_2H$ | |
| I-631 | J-4 | — | $CH_3$ | N | $OC_2H_5$ | $NHCH_3$ | |
| I-632 | J-4 | — | $CH_3$ | N | $OC_2H_5$ | $N(CH_3)_2$ | |
| I-633 | J-4 | — | $CH_3$ | N | $OC_2H_5$ | Cl | |
| I-634 | J-4 | — | $CH_3$ | N | $CH_3$ | $CH_3$ | |
| I-635 | J-4 | — | $CH_3$ | N | $CH_3$ | $C_2H_5$ | |
| I-636 | J-4 | — | $CH_3$ | N | $CH_3$ | $CF_3$ | |
| I-637 | J-4 | — | $CH_3$ | N | $CH_3$ | $OCF_2H$ | |
| I-638 | J-4 | — | $CH_3$ | N | $CH_3$ | $NHCH_3$ | |
| I-639 | J-4 | — | $CH_3$ | N | $CH_3$ | $N(CH_3)_2$ | |
| I-640 | J-4 | — | $CH_3$ | N | $CH_3$ | Cl | |
| I-641 | J-4 | — | $CH_3$ | N | $C_2H_5$ | $C_2H_5$ | |
| I-642 | J-4 | — | $CH_3$ | N | $C_2H_5$ | $CF_3$ | |
| I-643 | J-4 | — | $CH_3$ | N | $C_2H_5$ | $OCF_2H$ | |
| I-644 | J-4 | — | $CH_3$ | N | $C_2H_5$ | $NHCH_3$ | |
| I-645 | J-4 | — | $CH_3$ | N | $C_2H_5$ | Cl | |
| I-646 | J-4 | — | $CH_3$ | N | $CF_3$ | $CF_3$ | |
| I-647 | J-4 | — | $CH_3$ | N | $CF_3$ | $OCF_2H$ | |
| I-648 | J-4 | — | $CH_3$ | N | $CF_3$ | $NHCH_3$ | |
| I-649 | J-4 | — | $CH_3$ | N | $CF_3$ | $N(CH_3)_2$ | |
| I-650 | J-4 | — | $CH_3$ | N | $CF_3$ | Cl | |
| I-651 | J-4 | — | $CH_3$ | N | $OCF_2H$ | $OCF_2H$ | |
| I-652 | J-4 | — | $CH_3$ | N | $OCF_2H$ | $NHCH_3$ | |
| I-653 | J-4 | — | $CH_3$ | N | $OCF_2H$ | $N(CH_3)_2$ | |
| I-654 | J-4 | — | $CH_3$ | N | $OCF_2H$ | Cl | |
| I-655 | J-4 | — | $CH_3$ | N | $NHCH_3$ | $NHCH_3$ | |
| I-656 | J-4 | — | $CH_3$ | N | $NHCH_3$ | $N(CH_3)_2$ | |
| I-657 | J-4 | — | $CH_3$ | N | $NHCH_3$ | Cl | |
| I-658 | J-4 | — | $CH_3$ | N | $N(CH_3)_2$ | $N(CH_3)_2$ | |
| I-659 | J-4 | — | $CH_3$ | N | $N(CH_3)_2$ | Cl | |
| I-660 | J-4 | — | $CH_3$ | N | Cl | Cl | |

TABLE 2

Examples of compounds of the formula (I) having $J = J$-1;
$R^4 = R^5 = R^6 = R^7 = H$ and $R^{10} = 6$-$CH_3$:

| Ex. No. | J | E | $R^1$ | A | $R^2$ | $R^3$ | m.p. (°C.) |
|---|---|---|---|---|---|---|---|
| I-661 | J-1 | — | H | CH | $OCH_3$ | $OCH_3$ | |
| I-662 | J-1 | — | H | CH | $OCH_3$ | $OC_2H_5$ | |
| I-663 | J-1 | — | H | CH | $OCH_3$ | $CH_3$ | |
| I-664 | J-1 | — | H | CH | $OCH_3$ | $C_2H_5$ | |
| I-665 | J-1 | — | H | CH | $OCH_3$ | $CF_3$ | |
| I-666 | J-1 | — | H | CH | $OCH_3$ | $OCF_2H$ | |
| I-667 | J-1 | — | H | CH | $OCH_3$ | $NHCH_3$ | |
| I-668 | J-1 | — | H | CH | $OCH_3$ | $N(CH_3)_2$ | |
| I-669 | J-1 | — | H | CH | $OCH_3$ | Cl | |
| I-670 | J-1 | — | H | CH | $OC_2H_5$ | $OC_2H_5$ | |
| I-671 | J-1 | — | H | CH | $OC_2H_5$ | $CH_3$ | |
| I-672 | J-1 | — | H | CH | $OC_2H_5$ | $C_2H_5$ | |
| I-673 | J-1 | — | H | CH | $OC_2H_5$ | $CF_3$ | |
| I-674 | J-1 | — | H | CH | $OC_2H_5$ | $OCF_2H$ | |
| I-675 | J-1 | — | H | CH | $OC_2H_5$ | $NHCH_3$ | |
| I-676 | J-1 | — | H | CH | $OC_2H_5$ | $N(CH_3)_2$ | |
| I-677 | J-1 | — | H | CH | $OC_2H_5$ | Cl | |
| I-678 | J-1 | — | H | CH | $CH_3$ | $CH_3$ | |
| I-679 | J-1 | — | H | CH | $CH_3$ | $C_2H_5$ | |
| I-680 | J-1 | — | H | CH | $CH_3$ | $CF_3$ | |
| I-681 | J-1 | — | H | CH | $CH_3$ | $OCF_2H$ | |
| I-682 | J-1 | — | H | CH | $CH_3$ | $NHCH_3$ | |
| I-683 | J-1 | — | H | CH | $CH_3$ | $N(CH_3)_2$ | |
| I-684 | J-1 | — | H | CH | $CH_3$ | Cl | |
| I-685 | J-1 | — | H | CH | $C_2H_5$ | $C_2H_5$ | |
| I-686 | J-1 | — | H | CH | $C_2H_5$ | $CF_3$ | |
| I-687 | J-1 | — | H | CH | $C_2H_5$ | $OCF_2H$ | |
| I-688 | J-1 | — | H | CH | $C_2H_5$ | $NHCH_3$ | |
| I-689 | J-1 | — | H | CH | $C_2H_5$ | Cl | |
| I-690 | J-1 | — | H | CH | $CF_3$ | $CF_3$ | |
| I-691 | J-1 | — | H | CH | $CF_3$ | $OCF_2H$ | |
| I-692 | J-1 | — | H | CH | $CF_3$ | $NHCH_3$ | |
| I-693 | J-1 | — | H | CH | $CF_3$ | $N(CH_3)_2$ | |
| I-694 | J-1 | — | H | CH | $CF_3$ | Cl | |
| I-695 | J-1 | — | H | CH | $OCF_2H$ | $OCF_2H$ | |
| I-696 | J-1 | — | H | CH | $OCF_2H$ | $NHCH_3$ | |
| I-697 | J-1 | — | H | CH | $OCF_2H$ | $N(CH_3)_2$ | |
| I-698 | J-1 | — | H | CH | $OCF_2H$ | Cl | |
| I-699 | J-1 | — | H | CH | $NHCH_3$ | $NHCH_3$ | |
| I-700 | J-1 | — | H | CH | $NHCH_3$ | $N(CH_3)_2$ | |
| I-701 | J-1 | — | H | CH | $NHCH_3$ | Cl | |
| I-702 | J-1 | — | H | CH | $N(CH_3)_2$ | $N(CH_3)_2$ | |
| I-703 | J-1 | — | H | CH | $N(CH_3)_2$ | Cl | |
| I-704 | J-1 | — | H | CH | Cl | Cl | |
| I-705 | J-1 | — | H | N | $OCH_3$ | $OCH_3$ | |
| I-706 | J-1 | — | H | N | $OCH_3$ | $OC_2H_5$ | |

TABLE 2-continued

Examples of compounds of the formula (I) having J = J-1; $R^4 = R^5 = R^6 = R^7 = H$ and $R^{10} = 6\text{-}CH_3$:

| Ex. No. | J | E | $R^1$ | A | $R^2$ | $R^3$ | m.p. (°C.) |
|---|---|---|---|---|---|---|---|
| I-707 | J-1 | — | H | N | $OCH_3$ | $CH_3$ | |
| I-708 | J-1 | — | H | N | $OCH_3$ | $C_2H_5$ | |
| I-709 | J-1 | — | H | N | $OCH_3$ | $CF_3$ | |
| I-710 | J-1 | — | H | N | $OCH_3$ | $OCF_2H$ | |
| I-711 | J-1 | — | H | N | $OCH_3$ | $NHCH_3$ | |
| I-712 | J-1 | — | H | N | $OCH_3$ | $N(CH_3)_2$ | |
| I-713 | J-1 | — | H | N | $OCH_3$ | Cl | |
| I-714 | J-1 | — | H | N | $OC_2H_5$ | $OC_2H_5$ | |
| I-715 | J-1 | — | H | N | $OC_2H_5$ | $CH_3$ | |
| I-716 | J-1 | — | H | N | $OC_2H_5$ | $C_2H_5$ | |
| I-717 | J-1 | — | H | N | $OC_2H_5$ | $CF_3$ | |
| I-718 | J-1 | — | H | N | $OC_2H_5$ | $OCF_2H$ | |
| I-719 | J-1 | — | H | N | $OC_2H_5$ | $NHCH_3$ | |
| I-720 | J-1 | — | H | N | $OC_2H_5$ | $N(CH_3)_2$ | |
| I-721 | J-1 | — | H | N | $OC_2H_5$ | Cl | |
| I-722 | J-1 | — | H | N | $CH_3$ | $CH_3$ | |
| I-723 | J-1 | — | H | N | $CH_3$ | $C_2H_5$ | |
| I-724 | J-1 | — | H | N | $CH_3$ | $CF_3$ | |
| I-725 | J-1 | — | H | N | $CH_3$ | $OCF_2H$ | |
| I-726 | J-1 | — | H | N | $CH_3$ | $NHCH_3$ | |
| I-727 | J-1 | — | H | N | $CH_3$ | $N(CH_3)_2$ | |
| I-728 | J-1 | — | H | N | $CH_3$ | Cl | |
| I-729 | J-1 | — | H | N | $C_2H_5$ | $C_2H_5$ | |
| I-730 | J-1 | — | H | N | $C_2H_5$ | $CF_3$ | |
| I-731 | J-1 | — | H | N | $C_2H_5$ | $OCF_2H$ | |
| I-732 | J-1 | — | H | N | $C_2H_5$ | $NHCH_3$ | |
| I-733 | J-1 | — | H | N | $C_2H_5$ | Cl | |
| I-734 | J-1 | — | H | N | $CF_3$ | $CF_3$ | |
| I-735 | J-1 | — | H | N | $CF_3$ | $OCF_2H$ | |
| I-736 | J-1 | — | H | N | $CF_3$ | $NHCH_3$ | |
| I-737 | J-1 | — | H | N | $CF_3$ | $N(CH_3)_2$ | |
| I-738 | J-1 | — | H | N | $CF_3$ | Cl | |
| I-739 | J-1 | — | H | N | $OCF_2H$ | $OCF_2H$ | |
| I-740 | J-1 | — | H | N | $OCF_2H$ | $NHCH_3$ | |
| I-741 | J-1 | — | H | N | $OCF_2H$ | $N(CH_3)_2$ | |
| I-742 | J-1 | — | H | N | $OCF_2H$ | Cl | |
| I-743 | J-1 | — | H | N | $NHCH_3$ | $NHCH_3$ | |
| I-744 | J-1 | — | H | N | $NHCH_3$ | $N(CH_3)_2$ | |
| I-745 | J-1 | — | H | N | $NHCH_3$ | Cl | |
| I-746 | J-1 | — | H | N | $N(CH_3)_2$ | $N(CH_3)_2$ | |
| I-747 | J-1 | — | H | N | $N(CH_3)_2$ | Cl | |
| I-748 | J-1 | — | H | N | Cl | Cl | |
| I-749 | J-1 | — | $CH_3$ | N | $OCH_3$ | $OCH_3$ | |
| I-750 | J-1 | — | $CH_3$ | N | $OCH_3$ | $OC_2H_5$ | |
| I-751 | J-1 | — | $CH_3$ | N | $OCH_3$ | $CH_3$ | |
| I-752 | J-1 | — | $CH_3$ | N | $OCH_3$ | $C_2H_5$ | |
| I-753 | J-1 | — | $CH_3$ | N | $OCH_3$ | $CF_3$ | |
| I-754 | J-1 | — | $CH_3$ | N | $OCH_3$ | $OCF_2H$ | |
| I-755 | J-1 | — | $CH_3$ | N | $OCH_3$ | $NHCH_3$ | |
| I-756 | J-1 | — | $CH_3$ | N | $OCH_3$ | $N(CH_3)_2$ | |
| I-757 | J-1 | — | $CH_3$ | N | $OCH_3$ | Cl | |
| I-758 | J-1 | — | $CH_3$ | N | $OC_2H_5$ | $OC_2H_5$ | |
| I-759 | J-1 | — | $CH_3$ | N | $OC_2H_5$ | $CH_3$ | |
| I-760 | J-1 | — | $CH_3$ | N | $OC_2H_5$ | $C_2H_5$ | |
| I-761 | J-1 | — | $CH_3$ | N | $OC_2H_5$ | $CF_3$ | |
| I-762 | J-1 | — | $CH_3$ | N | $OC_2H_5$ | $OCF_2H$ | |
| I-763 | J-1 | — | $CH_3$ | N | $OC_2H_5$ | $NHCH_3$ | |
| I-764 | J-1 | — | $CH_3$ | N | $OC_2H_5$ | $N(CH_3)_2$ | |
| I-765 | J-1 | — | $CH_3$ | N | $OC_2H_5$ | Cl | |
| I-766 | J-1 | — | $CH_3$ | N | $CH_3$ | $CH_3$ | |
| I-767 | J-1 | — | $CH_3$ | N | $CH_3$ | $C_2H_5$ | |
| I-768 | J-1 | — | $CH_3$ | N | $CH_3$ | $CF_3$ | |
| I-769 | J-1 | — | $CH_3$ | N | $CH_3$ | $OCF_2H$ | |
| I-770 | J-1 | — | $CH_3$ | N | $CH_3$ | $NHCH_3$ | |
| I-771 | J-1 | — | $CH_3$ | N | $CH_3$ | $N(CH_3)_2$ | |
| I-772 | J-1 | — | $CH_3$ | N | $CH_3$ | Cl | |
| I-773 | J-1 | — | $CH_3$ | N | $C_2H_5$ | $C_2H_5$ | |
| I-774 | J-1 | — | $CH_3$ | N | $C_2H_5$ | $CF_3$ | |
| I-775 | J-1 | — | $CH_3$ | N | $C_2H_5$ | $OCF_2H$ | |
| I-776 | J-1 | — | $CH_3$ | N | $C_2H_5$ | $NHCH_3$ | |
| I-777 | J-1 | — | $CH_3$ | N | $C_2H_5$ | Cl | |
| I-778 | J-1 | — | $CH_3$ | N | $CF_3$ | $CF_3$ | |
| I-779 | J-1 | — | $CH_3$ | N | $CF_3$ | $OCF_2H$ | |
| I-780 | J-1 | — | $CH_3$ | N | $CF_3$ | $NHCH_3$ | |
| I-781 | J-1 | — | $CH_3$ | N | $CF_3$ | $N(CH_3)_2$ | |
| I-782 | J-1 | — | $CH_3$ | N | $CF_3$ | Cl | |
| I-783 | J-1 | — | $CH_3$ | N | $OCF_2H$ | $OCF_2H$ | |
| I-784 | J-1 | — | $CH_3$ | N | $OCF_2H$ | $NHCH_3$ | |
| I-785 | J-1 | — | $CH_3$ | N | $OCF_2H$ | $N(CH_3)_2$ | |
| I-786 | J-1 | — | $CH_3$ | N | $OCF_2H$ | Cl | |
| I-787 | J-1 | — | $CH_3$ | N | $NHCH_3$ | $NHCH_3$ | |
| I-788 | J-1 | — | $CH_3$ | N | $NHCH_3$ | $N(CH_3)_2$ | |
| I-789 | J-1 | — | $CH_3$ | N | $NHCH_3$ | Cl | |
| I-790 | J-1 | — | $CH_3$ | N | $N(CH_3)_2$ | $N(CH_3)_2$ | |
| I-791 | J-1 | — | $CH_3$ | N | $N(CH_3)_2$ | Cl | |
| I-792 | J-1 | — | $CH_3$ | N | Cl | Cl | |

TABLE 3

Examples of compounds of the formula (I) having J = J-3; $R^4 = R^5 = R^6 = R^7 = H$; $R^8 = CH_3$ and $R^{10} = Cl$:

| Ex. No. | J | E | $R^1$ | A | $R^2$ | $R^3$ | m.p. (°C.) |
|---|---|---|---|---|---|---|---|
| I-793 | J-3 | — | H | CH | $OCH_3$ | $OCH_3$ | 243(+) |
| I-794 | J-3 | — | H | CH | $OCH_3$ | $OC_2H_5$ | 117–120 187–190(+) |
| I-795 | J-3 | — | H | CH | $OCH_3$ | $CH_3$ | 188–194 214(+) |
| I-796 | J-3 | — | H | CH | $OCH_3$ | $C_2H_5$ | |
| I-797 | J-3 | — | H | CH | $OCH_3$ | $CF_3$ | |
| I-798 | J-3 | — | H | CH | $OCH_3$ | $OCF_2H$ | |
| I-799 | J-3 | — | H | CH | $OCH_3$ | $NHCH_3$ | |
| I-800 | J-3 | — | H | CH | $OCH_3$ | $N(CH_3)_2$ | |
| I-801 | J-3 | — | H | CH | $OCH_3$ | Cl | 177–178 200–201(+) |
| I-802 | J-3 | — | H | CH | $OC_2H_5$ | $OC_2H_5$ | 187–193 |
| I-803 | J-3 | — | H | CH | $OC_2H_5$ | $CH_3$ | |
| I-804 | J-3 | — | H | CH | $OC_2H_5$ | $C_2H_5$ | |
| I-805 | J-3 | — | H | CH | $OC_2H_5$ | $CF_3$ | |
| I-806 | J-3 | — | H | CH | $OC_2H_5$ | $OCF_2H$ | |
| I-807 | J-3 | — | H | CH | $OC_2H_5$ | $NHCH_3$ | |
| I-808 | J-3 | — | H | CH | $OC_2H_5$ | $N(CH_3)_2$ | |
| I-809 | J-3 | — | H | CH | $OC_2H_5$ | Cl | 173–175 218(+) |
| I-810 | J-3 | — | H | CH | $CH_3$ | $CH_3$ | 193–194 228–230(+) |
| I-811 | J-3 | — | H | CH | $CH_3$ | $C_2H_5$ | |
| I-812 | J-3 | — | H | CH | $CH_3$ | $CF_3$ | |
| I-813 | J-3 | — | H | CH | $CH_3$ | $OCF_2H$ | |
| I-814 | J-3 | — | H | CH | $CH_3$ | $NHCH_3$ | |
| I-815 | J-3 | — | H | CH | $CH_3$ | $N(CH_3)_2$ | |
| I-816 | J-3 | — | H | CH | $CH_3$ | Cl | 190 205(+) |
| I-817 | J-3 | — | H | CH | $C_2H_5$ | $C_2H_5$ | |
| I-818 | J-3 | — | H | CH | $C_2H_5$ | $CF_3$ | |
| I-819 | J-3 | — | H | CH | $C_2H_5$ | $OCF_2H$ | |
| I-820 | J-3 | — | H | CH | $C_2H_5$ | $NHCH_3$ | |
| I-821 | J-3 | — | H | CH | $C_2H_5$ | Cl | |
| I-822 | J-3 | — | H | CH | $CF_3$ | $CF_3$ | |
| I-823 | J-3 | — | H | CH | $CF_3$ | $OCF_2H$ | |
| I-824 | J-3 | — | H | CH | $CF_3$ | $NHCH_3$ | |
| I-825 | J-3 | — | H | CH | $CF_3$ | $N(CH_3)_2$ | |
| I-826 | J-3 | — | H | CH | $CF_3$ | Cl | |
| I-827 | J-3 | — | H | CH | $OCF_2H$ | $OCF_2H$ | |
| I-828 | J-3 | — | H | CH | $OCF_2H$ | $NHCH_3$ | |
| I-829 | J-3 | — | H | CH | $OCF_2H$ | $N(CH_3)_2$ | |
| I-830 | J-3 | — | H | CH | $OCF_2H$ | Cl | |
| I-831 | J-3 | — | H | CH | $NHCH_3$ | $NHCH_3$ | |
| I-832 | J-3 | — | H | CH | $NHCH_3$ | $N(CH_3)_2$ | |

TABLE 3-continued

Examples of compounds of the formula (I) having
J = J-3; $R^4 = R^5 = R^6 = R^7$ = H;
$R^8 = CH_3$ and $R^{10}$ = Cl:

| Ex. No. | J | E | $R^1$ | A | $R^2$ | $R^3$ | m.p. (°C.) |
|---|---|---|---|---|---|---|---|
| I-833 | J-3 | — | H | CH | $NHCH_3$ | Cl | |
| I-834 | J-3 | — | H | CH | $N(CH_3)_2$ | $N(CH_3)_2$ | |
| I-835 | J-3 | — | H | CH | $N(CH_3)_2$ | Cl | |
| I-836 | J-3 | — | H | CH | Cl | Cl | |
| I-837 | J-3 | — | H | N | $OCH_3$ | $OCH_3$ | 172 218$^{(+)}$ |
| I-838 | J-3 | — | H | N | $OCH_3$ | $OC_2H_5$ | |
| I-839 | J-3 | — | H | N | $OCH_3$ | $CH_3$ | 190–192$^{(+)}$ |
| I-840 | J-3 | — | H | N | $OCH_3$ | $C_2H_5$ | |
| I-841 | J-3 | — | H | N | $OCH_3$ | $CF_3$ | |
| I-842 | J-3 | — | H | N | $OCH_3$ | $OCF_2H$ | |
| I-843 | J-3 | — | H | N | $OCH_3$ | $NHCH_3$ | |
| I-844 | J-3 | — | H | N | $OCH_3$ | $N(CH_3)_2$ | |
| I-845 | J-3 | — | H | N | $OCH_3$ | Cl | |
| I-846 | J-3 | — | H | N | $OC_2H_5$ | $OC_2H_5$ | |
| I-847 | J-3 | — | H | N | $OC_2H_5$ | $CH_3$ | |
| I-848 | J-3 | — | H | N | $OC_2H_5$ | $C_2H_5$ | |
| I-849 | J-3 | — | H | N | $OC_2H_5$ | $CF_3$ | |
| I-850 | J-3 | — | H | N | $OC_2H_5$ | $OCF_2H$ | |
| I-851 | J-3 | — | H | N | $OC_2H_5$ | $NHCH_3$ | |
| I-852 | J-3 | — | H | N | $OC_2H_5$ | $N(CH_3)_2$ | |
| I-853 | J-3 | — | H | N | $OC_2H_5$ | Cl | |
| I-854 | J-3 | — | H | N | $CH_3$ | $CH_3$ | 151–153 130–135$^{(+)}$ |
| I-855 | J-3 | — | H | N | $CH_3$ | $C_2H_5$ | |
| I-856 | J-3 | — | H | N | $CH_3$ | $CF_3$ | |
| I-857 | J-3 | — | H | N | $CH_3$ | $OCF_2H$ | |
| I-858 | J-3 | — | H | N | $CH_3$ | $NHCH_3$ | |
| I-859 | J-3 | — | H | N | $CH_3$ | $N(CH_3)_2$ | |
| I-860 | J-3 | — | H | N | $CH_3$ | Cl | |
| I-861 | J-3 | — | H | N | $C_2H_5$ | $C_2H_5$ | |
| I-862 | J-3 | — | H | N | $C_2H_5$ | $CF_3$ | |
| I-863 | J-3 | — | H | N | $C_2H_5$ | $OCF_2H$ | |
| I-864 | J-3 | — | H | N | $C_2H_5$ | $NHCH_3$ | |
| I-865 | J-3 | — | H | N | $C_2H_5$ | Cl | |
| I-866 | J-3 | — | H | N | $CF_3$ | $CF_3$ | |
| I-867 | J-3 | — | H | N | $CF_3$ | $OCF_2H$ | |
| I-868 | J-3 | — | H | N | $CF_3$ | $NHCH_3$ | |
| I-869 | J-3 | — | H | N | $CF_3$ | $N(CH_3)_2$ | |
| I-870 | J-3 | — | H | N | $CF_3$ | Cl | |
| I-871 | J-3 | — | H | N | $OCF_2H$ | $OCF_2H$ | |
| I-872 | J-3 | — | H | N | $OCF_2H$ | $NHCH_3$ | |
| I-873 | J-3 | — | H | N | $OCF_2H$ | $N(CH_3)_2$ | |
| I-874 | J-3 | — | H | N | $OCF_2H$ | Cl | |
| I-875 | J-3 | — | H | N | $NHCH_3$ | $NHCH_3$ | |
| I-876 | J-3 | — | H | N | $NHCH_3$ | $N(CH_3)_2$ | |
| I-877 | J-3 | — | H | N | $NHCH_3$ | Cl | |
| I-878 | J-3 | — | H | N | $N(CH_3)_2$ | $N(CH_3)_2$ | |
| I-879 | J-3 | — | H | N | $N(CH_3)_2$ | Cl | |
| I-880 | J-3 | — | H | N | Cl | Cl | |
| I-881 | J-3 | — | $CH_3$ | N | $OCH_3$ | $OCH_3$ | 172–173 110–114$^{(+)}$ |
| I-882 | J-3 | — | $CH_3$ | N | $OCH_3$ | $OC_2H_5$ | |
| I-883 | J-3 | — | $CH_3$ | N | $OCH_3$ | $CH_3$ | |
| I-884 | J-3 | — | $CH_3$ | N | $OCH_3$ | $C_2H_5$ | |
| I-885 | J-3 | — | $CH_3$ | N | $OCH_3$ | $CF_3$ | |
| I-886 | J-3 | — | $CH_3$ | N | $OCH_3$ | $OCF_2H$ | |
| I-887 | J-3 | — | $CH_3$ | N | $OCH_3$ | $NHCH_3$ | |
| I-888 | J-3 | — | $CH_3$ | N | $OCH_3$ | $N(CH_3)_2$ | |
| I-889 | J-3 | — | $CH_3$ | N | $OCH_3$ | Cl | |
| I-890 | J-3 | — | $CH_3$ | N | $OC_2H_5$ | $OC_2H_5$ | |
| I-891 | J-3 | — | $CH_3$ | N | $OC_2H_5$ | $CH_3$ | |
| I-892 | J-3 | — | $CH_3$ | N | $OC_2H_5$ | $C_2H_5$ | |
| I-893 | J-3 | — | $CH_3$ | N | $OC_2H_5$ | $CF_3$ | |
| I-894 | J-3 | — | $CH_3$ | N | $OC_2H_5$ | $OCF_2H$ | |
| I-895 | J-3 | — | $CH_3$ | N | $OC_2H_5$ | $NHCH_3$ | |
| I-896 | J-3 | — | $CH_3$ | N | $OC_2H_5$ | $N(CH_3)_2$ | |
| I-897 | J-3 | — | $CH_3$ | N | $OC_2H_5$ | Cl | |
| I-898 | J-3 | — | $CH_3$ | N | $CH_3$ | $CH_3$ | |
| I-899 | J-3 | — | $CH_3$ | N | $CH_3$ | $C_2H_5$ | |
| I-900 | J-3 | — | $CH_3$ | N | $CH_3$ | $CF_3$ | |
| I-901 | J-3 | — | $CH_3$ | N | $CH_3$ | $OCF_2H$ | |
| I-902 | J-3 | — | $CH_3$ | N | $CH_3$ | $NHCH_3$ | |
| I-903 | J-3 | — | $CH_3$ | N | $CH_3$ | $N(CH_3)_2$ | |
| I-904 | J-3 | — | $CH_3$ | N | $CH_3$ | Cl | |
| I-905 | J-3 | — | $CH_3$ | N | $C_2H_5$ | $C_2H_5$ | |
| I-906 | J-3 | — | $CH_3$ | N | $C_2H_5$ | $CF_3$ | |
| I-907 | J-3 | — | $CH_3$ | N | $C_2H_5$ | $OCF_2H$ | |
| I-908 | J-3 | — | $CH_3$ | N | $C_2H_5$ | $NHCH_3$ | |
| I-909 | J-3 | — | $CH_3$ | N | $C_2H_5$ | Cl | |
| I-910 | J-3 | — | $CH_3$ | N | $CF_3$ | $CF_3$ | |
| I-911 | J-3 | — | $CH_3$ | N | $CF_3$ | $OCF_2H$ | |
| I-912 | J-3 | — | $CH_3$ | N | $CF_3$ | $NHCH_3$ | |
| I-913 | J-3 | — | $CH_3$ | N | $CF_3$ | $N(CH_3)_2$ | |
| I-914 | J-3 | — | $CH_3$ | N | $CF_3$ | Cl | |
| I-915 | J-3 | — | $CH_3$ | N | $OCF_2H$ | $OCF_2H$ | |
| I-916 | J-3 | — | $CH_3$ | N | $OCF_2H$ | $NHCH_3$ | |
| I-917 | J-3 | — | $CH_3$ | N | $OCF_2H$ | $N(CH_3)_2$ | |
| I-918 | J-3 | — | $CH_3$ | N | $OCF_2H$ | Cl | |
| I-919 | J-3 | — | $CH_3$ | N | $NHCH_3$ | $NHCH_3$ | |
| I-920 | J-3 | — | $CH_3$ | N | $NHCH_3$ | $N(CH_3)_2$ | |
| I-921 | J-3 | — | $CH_3$ | N | $NHCH_3$ | Cl | |
| I-922 | J-3 | — | $CH_3$ | N | $N(CH_3)_2$ | $N(CH_3)_2$ | |
| I-923 | J-3 | — | $CH_3$ | N | $N(CH_3)_2$ | Cl | |
| I-924 | J-3 | — | $CH_3$ | N | Cl | Cl | |

TABLE 4

Examples of compounds of the formula (1) having
$R^1 = R^4 = R^5 = R^6 = R^7 = R^{10}$ = H

| Ex. No. | J | E | A | $R^2$ | $R^3$ | $R^8$ | m.p. (°C.) |
|---|---|---|---|---|---|---|---|
| I-925 | J-1 | — | CH | $OC_6H_5$ | $CH_3$ | — | 105–109 186–190$^{(+)}$ |
| I-926 | J-1 | — | CH | Cl | $OCH_2CF_3$ | — | 111 120–124$^{(+)}$ |
| I-927 | J-2 | — | N | $N(CH_3)_2$ | $OCH_2CF_3$ | — | 158 |
| I-928 | J-2 | — | CH | Cl | $OCH_2CF_3$ | — | 204–205 207$^{(+)}$ |
| I-929 | J-3 | — | CH | Cl | $OCH_2CF_3$ | $CH_3$ | 110 214–218$^{(+)}$ |
| I-930 | J-3 | — | N | $N(CH_3)_2$ | $OCH_2CF_3$ | $CH_3$ | 183–184 214–216$^{(+)}$ |
| I-931 | J-3 | — | CH | $CH_3$ | $OC_6H_5$ | $CH_3$ | 195–198 248–249$^{(+)}$ |
| I-932 | J-4 | — | CH | Cl | $OCH_2CF_3$ | — | 115–118 166$^{(+)}$ |
| I-933 | J-4 | — | N | $N(CH_3)_2$ | $OCH_2CF_3$ | — | 173–174 |
| I-934 | J-4 | — | CH | $CH_3$ | $OC_6H_5$ | — | 104–108 184$^{(+)}$ |

Salts of Compounds of the Formula (I):

EXAMPLE I-397-a

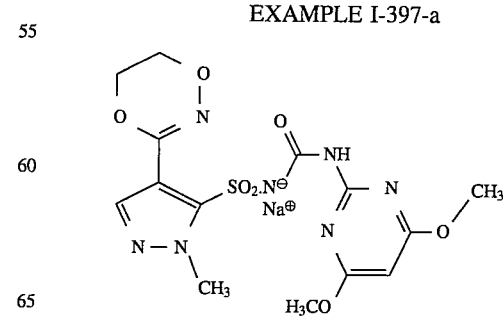

0.5 g (0.01 mol) of 80% sodium hydroxide powder are added, whilst stirring, to a mixture consisting of 4.3 g (0.01 mol) of N-(4,6-dimethoxypyrimidin-2-yl)-N'-(1-methyl-4-(5,6-dihydro-[1,4,2]-dioxazin-3-yl)pyrazole-5-sulphonyl)-urea and 100 ml of toluene. The mixture is stirred at 20° C. for 15 hours; the crystalline product is subsequently isolated by filtering off with suction.

4.5 g (99% of theory) of N-(4,6-dimethoxypyrimidin-2-yl)-N'-(1-methyl-4-(5,6-dihydro-[1,4,2]-dioxazin-3-yl)pyrazole-5-sulphonyl)-urea Na salt are obtained with a melting point of 250° C. (with decomposition).

The following are obtained in an analogous manner:

EXAMPLE I-89-a

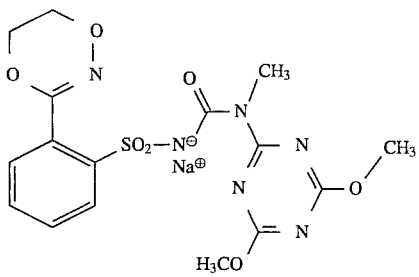

N-(4,6-Dimethoxy-1,3,5-triazin-2-yl)-N-methyl-N'-(2-(5,6-dihydro-[1,4,2]-dioxazin-3-yl)benzenesulphonyl)-urea Na salt. Melting point 146°–149° C.

EXAMPLE I-617-a

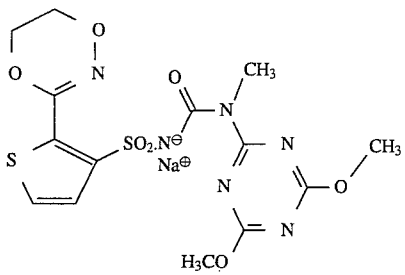

N-(4,6-Dimethoxy-1,3,5-triazin-2-yl)-N-methyl-N'-(2-(5,6-dihydro-[1,4,2]-dioxazin-3-yl)-thiophene-3-sulphonyl)-urea Na salt. Melting point 97°–100° C.

Starting Compounds of the Formula (II)

EXAMPLE (II-1)

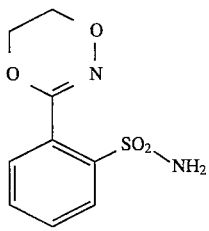

Process (d)

Chlorine is passed, at 0° C., into a mixture consisting of 22.7 g (0.0795 mol) of 1-benzylthio-2-(5,6-dihydro-[1,4,2]-dioxazin-3-yl)-benzene in 150 ml of dichloromethane and 70 g of sodium dihydrogen phosphate hydrate in 150 ml of water until it is saturated. Subsequently, the phases are separated, the organic phase is dried, and the solvent is stripped off under reduced pressure. The sulphonyl chloride which is formed under these circumstances is taken up in 50 ml of absolute tetrahydrofuran and this solution is added dropwise at −40° C. to a mixture consisting of 500 ml of tetrahydrofuran and 50 ml of ammonia. Stirring of the mixture is continued at room temperature for a further 2 hours and the precipitated salts are then filtered off with suction. The filtrate is freed from the solvent under reduced pressure and the residue is chromatographed (eluents: 1. dichloromethane, 2. cyclohexane/ethyl acetate 1:1). 11.5 g (60% of theory) of 2-(5,6-dihydro-[1,4,2]-dioxazin-3-yl)-benzenesulphonamide are obtained as a pale yellow solid. Melting point: 131°–133° C.

The following are obtained in an analogous manner:

EXAMPLE II-2

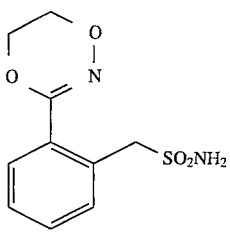

2-(5,6-Dihydro-[1,4,2]-dioxazin-3-yl)phenylmethanesulphonamide. Melting point: . . . °C.

EXAMPLE II-3

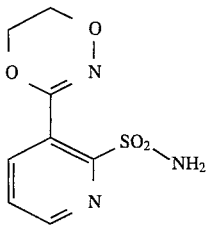

3-(5,6-Dihydro-[1,4,2]-dioxazin-3-yl)-pyridine-2-sulphonamide. Melting point: 170° C.

EXAMPLE II-4

Process (e)

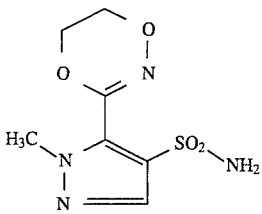

6.28 g (0.112 mol) of potassium hydroxide in 100 ml of methanol are added dropwise, at room temperature, to a mixture of 7.78 g (0.112 mol) of hydroxylamine hydrochloride and 150 ml of methanol. Subsequently, 13.1 g (0.056 mol) of 1-methyl-5-ethoxycarbonylpyrazole-4-sulphonamide are added in portions at room temperature. The mixture is stirred at room temperature overnight, and subsequently at 40° C. for 2 hours and at 60° C. for a further 2 hours. 3.14 g (0.056 mol) of potassium hydroxide in 50 ml of methanol are added dropwise, and the mixture is then stirred at 60° C. for a further 2 hours. 7.74 g (0.056 mol) of potassium carbonate are then added, 50.5 g (0.25 mol) of 1,2-dibromoethane (BrCH₂CH₂Br) are added dropwise, and the mixture is subsequently left stirring at 60° C. overnight. Subsequently, the solvent is distilled off under reduced pressure. The residue is partitioned between methylene chloride and water. The organic phase is dried and the solvent is distilled off under reduced pressure. The residue is chromatographed (eluent: cyclohexane/ethyl acetate 2:3).

5.91 g (43% of theory) of 1-methyl-5-(5,6-dihydro-[1,4,2]-dioxazin-3-yl)pyrazole4-sulphonamide are obtained as a pale yellow solid. Melting point: 126°–130° C.

The following is obtained in an analogous manner:

EXAMPLE II-5

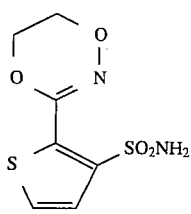

2-(5,6-Dihydro-[1,4,2]-dioxazin-3-yl)thiophene-3-sulphonamide. Melting point: 180°–184° C.

Starting Compounds of the Formula (VII)

EXAMPLE (VII-1)

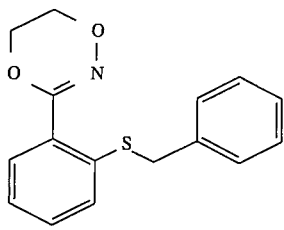

160 g (2.86 mol) of potassium hydroxide in 700 ml of methanol are added dropwise, at room temperature, to a mixture of 98.7 g (1.42 mol) of hydroxylamine hydrochloride and 700 ml of methanol. Subsequently, 184 g (0.712 mol) of methyl 2-(benzylthio)benzoate are added in portions at room temperature. The mixture is stirred at 40° C. overnight. 98.1 g (0.712 mol) of potassium carbonate are then added, 601 g (3.20 mol) of 1,2odibromoethane are added dropwise, and the mixture is left stirring at 60° C. overnight. Subsequently, the solvent is distilled off under reduced pressure. The residue is partitioned between methylene chloride and water. The organic phase is dried and the solvent is distilled off under reduced pressure. The residue is stirred up with absolute ethyl alcohol. The solid is filtered off with suction and dried under high vacuum.

43.1 g (2 1% of theory) of 1-benzylthio-2-(5,6-dihydro-[1,4,2]-dioxazin-3-yl)benzene are obtained as a pale yellow solid. Melting point: 73°–77° C.

The following is obtained in an analogous manner:

EXAMPLE VII-2

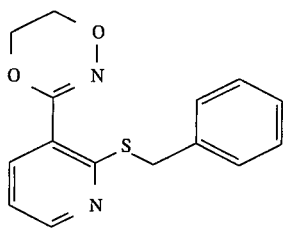

2-Benzylthio-3-(5,6-dihydro-[1,4,2]-dioxazin-3-yl)pyridine. Melting point: 65°–67.5° C.

Application Examples

In the following application examples, the compounds listed below are taken as compounds for comparison:

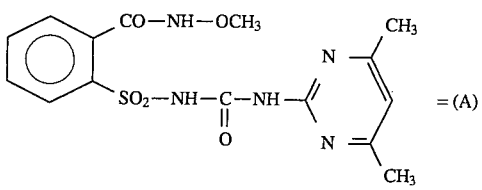

N-(4,6-Dimethylpyrimidin-2-yl)-N'-(2-methoxyaminocarbonyl-phenylsulphonyl)urea; and

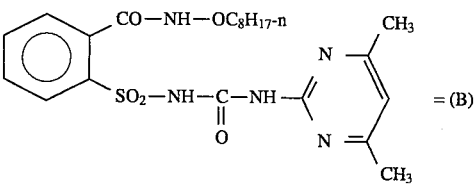

N-(4,6-dimethylpyrimidin-2-yl)-N'-(2-n-octyloxyaminocarbonyl-phenylsulphonyl)urea, (both known from DE-A-3 516 435, Examples 1 and 2, respectively).

EXAMPLE A

Pre-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:
0%=no action (like untreated control)
100%=total destruction A clear superiority in activity as compared with the state of the art is shown in this test by, for example, the compounds according to the following preparation examples: (I-1), (I-9), (I-18), (I-47).

EXAMPLE B

Post-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control.

The figures denote:
0%=no action (like untreated control)
100%=total destruction A clear superiority in activity as compared with the state of the art is shown in this test by, for example, the compounds according to the following preparation examples: (I-1), (I-18), (I-47), (I-89a), (I-397), (I-414), (I-485).

It will be appreciated that the instant specification and claims are set forth by way of illustration and not limitation, and that various modifications and changes may be made without departing from the spirit and scope of the present invention.

We claim:

1. An N-triazinyl-N'-(het)arylsulphonyl-urea of the formula

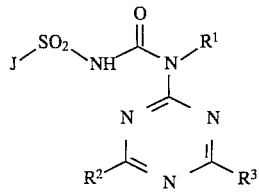

$R^1$ is hydrogen or a radical selected from the group consisting of optionally substituted alkyl, optionally substituted alkoxy, optionally substituted alkoxyalkyl, optionally substituted alkenyl, optionally substituted alkinyl, cycloalkyl, cycloalkylalkyl, aralkyl, and aryl, wherein said substituent is halogen, $R^2$ is hydrogen or halogen, or is alkyl, alkoxy, alkylthio, alkylamino or dialkylamino having in each group 1 to 6 carbon atoms optionally substituted by halogen, $R^3$ is hydrogen or halogen, or is alkyl, alkoxy, alkylthio, alkylamino or dialkylamino having in each alkyl group 1 to 6 carbon atoms optionally substituted by halogen, and J is a member selected from the group consisting of

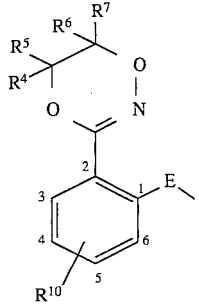

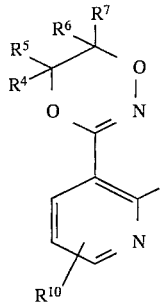

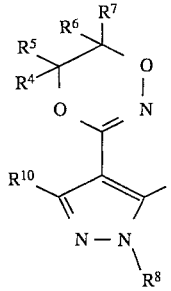

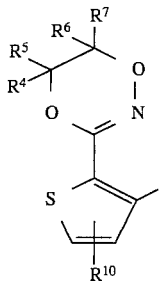

wherein

E is a direct linkage, alkylene, oxygen, alkylamino or sulphur, $R^4$, $R^5$, $R^6$ and $R^7$ each independently is hydrogen, halogen, cyano or thiocyanato, or is alkyl, alkoxy, alkylthio, alkylsulphinyl, alkylsulphonyl, alkylamino, alkylcarbonyl, alkoxycarbonyl or alkylaminocarbonyl having in each alkyl group 1 to 3 carbon atoms optionally substituted by halogen, $R^8$ is hydrogen, or a radical selected from the group consisting of alkyl, alkenyl, alkinyl, cycloalkyl, cycloalkylalkyl, aralkyl and aryl, or C(=O) $R^9$, wherein $R^9$ is hydrogen, or alkyl, aryl, alkoxy, alkylamino or dialkylamino, and $R^{10}$ is hydrogen, halogen, cyano or thiocyanato, or is alkyl, alkoxy, alkylthio, alkylsulphinyl, alkylsulphonyl, alkylamino, alkylcarbonyl, alkoxycarbonyl or alkylaminocarbonyl having in each alkyl group 1 to 3 carbon atoms optionally substituted by halogen,
wherein, unless otherwise specified, the alkyl, alkylene, alkenyl and alkinyl groups have up to 6 carbon atoms, the cycloalkyl groups 3 to 6 carbon atoms and the aryl groups 6 to 10 carbon atoms, or a salt thereof.

2. A sulphonylurea or salt thereof according to claim 1, wherein, unless otherwise specified, the alkyl, alkylene, alkenyl and alkinyl groups have up to 3 carbon atoms.

3. A sulphonylurea or salt thereof according to claim 2, wherein $R^1$ is hydrogen, methyl, ethyl, methoxy, methoxymethyl or ethoxy, $R^2$ is hydrogen, chlorine, methyl, ethyl, trifluoromethyl, methoxy, ethoxy, difluoromethoxy, methylthio, methylamino or dimethylamino, $R^3$ is hydrogen, chlorine, methyl, ethyl, trifluoromethyl, methoxy, ethoxy, difluoromethoxy, methylthio, methylamino or dimethylamino, E is a direct linkage, methylene, oxygen, $C_1$–$C_2$-alkylamino or sulphur, $R^4$, $R^5$, $R^6$ and $R^7$ each independently is hydrogen, fluorine, chlorine or cyano, or is optionally chlorine- or fluorine-substituted methyl, methylthio, methylsulphinyl, methylsulphonyl, methoxycarbonyl or ethoxycarbonyl, $R^8$ is hydrogen, methyl, ethyl, phenyl or benzyl, and $R^{10}$ is hydrogen, fluorine, chlorine; bromine or cyano, or is optionally chlorine- or fluorine-substituted methyl, methoxy, ethoxy, methylthio, ethylthio, methylsulphinyl, ethylsulphinyl, methylsulphonyl, ethylsulphonyl, methylamino or dimethylamino.

4. A sulphonylurea according to claim 1, wherein such compound is N-(4-methoxy-6-methyl-1,3,5-triazin-2-yl)-$N^1$-(2-(5,6-dihydro-[1,4,2]-dioxazin-3-yl)benzenesulphonyl)-urea of the formula

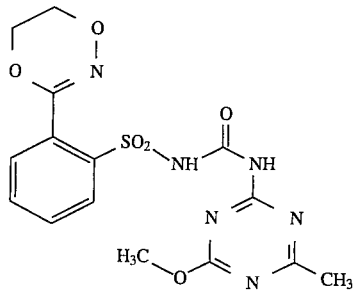

or a salt thereof.

5. A herbicidal composition comprising a herbicidally effective amount of a compound or salt thereof according to claim 1 and a diluent.

6. A method of combatting unwanted vegetation which comprises applying to such vegetation or to a locus from which it is desired to exclude such vegetation a herbicidally effective amount of a compound or salt thereof according to claim 1.

7. A method of combatting unwanted vegetation which comprises applying to such vegetation or to a locus from which it is desired to exclude such vegetation a herbicidally effective amount of a compound or salt thereof according to claim 4.

* * * * *